US008969653B2

(12) United States Patent
Gho et al.

(10) Patent No.: US 8,969,653 B2
(45) Date of Patent: Mar. 3, 2015

(54) EXTRACELLULAR VESICLES DERIVED FROM GRAM-POSITIVE BACTERIA, AND USE THEREOF

(75) Inventors: Yong Song Gho, Pohang-si (KR); Yoon Keun Kim, Pohang-si (KR); Eun Young Lee, Pohang-si (KR); Sung Wook Hong, Sokcho-si (KR); Ji Hyun Kim, Yeongju-si (KR); Seng Jin Choi, Pohang-si (KR)

(73) Assignee: Aeon Medix Inc., Gyeongsangbuk-Do (KR)

( * ) Notice: Subject to any disclaimer, the term of this patent is extended or adjusted under 35 U.S.C. 154(b) by 47 days.

(21) Appl. No.: 13/394,113

(22) PCT Filed: Aug. 26, 2010

(86) PCT No.: PCT/KR2010/005721
§ 371 (c)(1),
(2), (4) Date: Mar. 2, 2012

(87) PCT Pub. No.: WO2011/027990
PCT Pub. Date: Mar. 10, 2011

(65) Prior Publication Data
US 2012/0159658 A1 Jun. 21, 2012

Related U.S. Application Data

(63) Continuation-in-part of application No. 13/393,808, filed as application No. PCT/KR2010/004747 on Jul. 20, 2010.

(30) Foreign Application Priority Data

Sep. 1, 2009 (KR) ........................ 10-2009-0082220
Sep. 4, 2009 (KR) ........................ 10-2009-0083621
Mar. 23, 2010 (WO) ................ PCT/KR2010/001787

(51) Int. Cl.
*A61K 39/02* (2006.01)
*A01K 67/027* (2006.01)
*C12P 1/04* (2006.01)

(52) U.S. Cl.
CPC ........... *C12P 1/04* (2013.01); *A01K 2267/0375* (2013.01); *A01K 2207/00* (2013.01)
USPC .............. 800/9; 424/234.1; 424/780; 435/23; 435/29; 435/317.1; 435/7.92

(58) Field of Classification Search
CPC .................. A01K 2207/00; A01K 2267/0375; C12P 1/04
See application file for complete search history.

(56) References Cited

U.S. PATENT DOCUMENTS 5,403,718 A 4/1995 Dorward et al.
7,384,645 B2 6/2008 Foster et al.
2003/0059444 A1 3/2003 Zollinger et al.
2005/0013831 A1 1/2005 Foster
2006/0166344 A1 7/2006 Pizza et al.
2007/0087017 A1* 4/2007 Olivieri et al. ............. 424/250.1
2007/0166333 A1 7/2007 Niebla Perez et al.
2008/0233154 A1 9/2008 Berthet et al.
2010/0143418 A1 6/2010 Contorni et al.
2011/0251156 A1 10/2011 Shen et al.
2011/0312510 A1* 12/2011 Mak et al. ........................ 506/8

FOREIGN PATENT DOCUMENTS

| CN | 1688334 A | 10/2005 |
|---|---|---|
| JP | 2007-533729 A | 11/2007 |
| WO | 97/05899 A2 | 2/1997 |
| WO | 0109350 A2 | 2/2001 |
| WO | 2004/014417 A2 | 2/2004 |
| WO | 2005-004925 A1 | 1/2005 |
| WO | 2005/035733 A2 | 4/2005 |
| WO | 2007/144316 A2 | 12/2007 |
| WO | 2009/030093 A1 | 3/2009 |
| WO | 2011/127302 A2 | 10/2011 |

OTHER PUBLICATIONS

Eda, et al., "Extracellular membranous structures in a stable L-form of *Staphylococcus aureus*", Journal of General Microbiology, 1977, vol. 103, No. 1, pp. 189-191.
Mashburn-Warren, et al, Special delivery: vesicle trafficking in prokaryotes:, Molecular Microbiology, Wiley Blackwell-Oxford, 2006, pp. 839-846.
Lee, et al., "Gram-positive bacteria produce membrane vesicles: Proteomics-based characterization of *Staphylococcus aureus*-derived membrane vesicles", Proteomics, 2009, vol. 9, No. 24, pp. 5425-5436.
Supplementary European Search Report dated Oct. 10, 2013 of the corresponding European Patent Application No. 10 813 899.1.
Dorward, et al., "DNA is Packaged within Membrane-Derived Vesicles of Gram-Negative but not Gram-Positive Bacteria", Applied and Environmental Microbiology, Jun. 1990, vol. 56. No. 6, pp. 1960-1962.
Kim, et al., "Extracellular Membrane Vesicles from Tumor Cells Promote Angiogenesis via Sphingomyelin", Cancer Research, 2002, vol. 62, No. 21, pp. 6312-6317.
Rodrigues, et al., "Extracellular Vesicles Produced by *Cryptococus neoformans* Contain Protein Components Associated with Virulence", Eukaryotic Cell, Jan. 2008, vol. 7, No. 1, pp. 58-67.

(Continued)

*Primary Examiner* — Doug Schultz
(74) *Attorney, Agent, or Firm* — Knobbe, Martens, Olson & Bear, LLP

(57) ABSTRACT

The present application relates to extracellular vesicles (EVs) derived from gram-positive bacteria. In detail, the present application provides animal models of disease using extracellular vesicles derived from gram-positive bacteria, provides a method for screening an active candidate substance which is capable of preventing or treating diseases through the animal models of disease, provides vaccines for preventing or treating diseases caused by extracellular vesicles derived from gram-positive bacteria, and provides a method for diagnosing the causative factors of diseases caused by gram-positive bacteria using extracellular vesicles.

17 Claims, 28 Drawing Sheets

(56) References Cited

OTHER PUBLICATIONS

Kuehn, et al., "Bacterial outer membrane vesicles and the host-pathogen interaction", Genes & Development, 2005, vol. 19, No. 22, pp. 2645-2655.
International Search Report issued on Jun. 10, 2011 for International Application No. PCT/KR2010/005721—5 pages.
Alaniz et al, "Membrane vesicles are immunogenic facsimiles of *Salmonella typhimurium* that potently activate dendritic cells, prime B and T cell responses, and stimulate protective immunity in vivo", Journal of Immunology, 2007, vol. 179, No. 11, pp. 7692-7701.
Annane et al. "Septick Shock", Lancet, 2005, 365-63-78.
Bjerre et al., "Complement activation induced by purified *Neisseria meningitidis* lipopolysaccharide (LPS), outer membrane vesicles, whole bacteria, and an LPS-free mutant", The Journal of Infectious Disease, 2002, vol. 185, No. 2, pp. 220-228.
Blanque, et al., "Increases in osteocalcin after ovariectomy are amplified by LPS injection: strain differences in bone remodeling," Gen Pharmacol, 1998, vol. 30, No. 1, pp. 51-56.
Lee, et al., Proteomics in gram-negative bacterial outer membrane vesicles. Mass. Spectrom. Rev. 2008;27 (6):535-555.
Buras et al., "Animal models of sepsis: setting the stage", Nat. Rev. Drug. Discov. 2005;4(10), pp. 854-865.
Japanese Office Action dated Aug. 15, 2014 for corresponding JP Application No. 2012-527808.
Chaffer et al. "Vaccination of turkey poults against pathogenic *Escherichia coli*", Avian Pathology, 1997, 26:377-390.
Chin, "Intestinal Endotoxemia (ITEM) and Medium Heptitis", J Clini Hepatol, Oct. 2008, vol. 24, No. 5, pp. 388-391 (with English Abstract).
Chinese Office Action dated Feb. 14, 2014 of corresponding Chines patent application No. 201080038540.9-8.
Eckburg et al, "Diversity of the Human Intestinal Microbial Flora", Science, 2005, vol. 308, No. 5278, pp. 1635-1638.
Extended European Search Report dated Apr. 10, 2014 of the corresponding European Patent Application No. 10813880.1-20 pages.
Girard et al., "A review of vaccine research and development: meningococcal disease", Vaccine. 2006;24(22), pp. 4692-4700.
Hellman, "Bacterial peptidoglycan-associated lipoprotein is released into the bloodstream in gram-negative sepsis and causes inflammation and death in mice", J. Biol. Chem. 2002; 19;277(1 6), pp. 14274-14280.
Henry et al, "Improved methods for producing outer membrane vesicles in Gram-negative bacteria", Research in Microbiology, 2004, vol. 155, No. 6, pp. 437-446.
Heo, et al., "LPS induces inflammatory responses in human aortic vascular smooth muscle cells via Toll-like receptor 4 expression and nitric oxide production," Immunology Letters., 2008, vol. 120, No. 1-2, pp. 57-64.
Hoist et al. "Properties and clinical performance of vaccines containing outer membrane vesicles from *Neisseria meningitidis*", Vaccine, 2009, 27 Supp2:B3-B12.
International Search Report dated Jun. 3, 2011 of PCT/KR2010/004747 which is the parent application—6 pages.
Japanese Office Action dated Oct. 2, 2013 of the corresponding Japanese Patent Application No. 2012-527808.
Kang et al., "Extracellular Vesicles Derived from Gut Microbiota, Especially *Akkermasia muciniphila*, Protect the Progression of Dextran Sulfate Sodium-Induced Colitis", PLOS ONE, 2013, vol. 8, No. 10.
Kesty et al., "Enterotoxigenic *Escherichia coli* vesicles target toxin delivery into mammalian cells", The EMBO Journal, 2004, vol. 23, No. 23, pp. 4538-4549.
Kim et al., "Engineered Bacterial Outer Membrane Vesicles with Enhanced Functionality", Journal of Molecular Biology, 2008, vol. 308, No. 1, pp. 51-66.
Kim et al., "Outer Membrane Vesicles Derived from *Escherichia coli* Up-Regulate Expression of Endothelial Cell Adhesion Molecules In Vitro and In Vivo", PLOS ONE, 2013, vol. 8, No. 3.
Leduc et al., "Outer Membrane-associated Deoxyribonuclease Activity of *Porphyromonas gingivalis*", Anaerobe, 1995, vol. 1, No. 2, pp. 129-134.

Lee et al., "Global proteomic profiling of native outer membrane vesicles derived from *Escherichia coli*" Proteomics, 2007, vol. 7, No. 17, pp. 3143-3153.
Lepper et al., "Clinical implications of antibiotic-induced endotoxin release in septic shock", Intensive Care Med, 2002, 28:824-833.
Levy, et al., "2001 SCCM/ESICM/ACCP/ATS/SIS International Sepsis Definitions Conference", Crit.Care. Med. 2003, vol. 31, No. 4, pp. 1250-1256.
Lolis, et al., "Therapeutic approaches to innate immunity: severe sepsis and septic shock", Nature Reviews, Drug Discovery, 2003, vol. 2 No. 8, pp. 635-645.
Mirlashari, et al., "Outer membrane vesicles from *Neisseria meningitidis*: effects on cytokine production in human whole blood", Cytokine, Jan. 21, 2001, vol. 13, No. 2, pp. 91-97.
Muller et al., "Identification of Unconventional Intestinal Pathogenic *Escherichia coli* Isolates Expressing Intermediate Virulence Factor Profiles by Using a Novel Single-Step Multiplex PCR", Applied and Environmental Microbiology, 2007, 73:3380-3390.
Munford, "Severe sepsis and septic shock: the role of gram-negative bacteremia" Annu. Rev.Pathol. 2006;1:467-496.
Namork, et al., "Fatal meningococcal septicaemia with blebbing meningococcus", The Lancet. Nov. 30, 2002, vol. 360, (9347), p. 1741.
Neilsen, et al., "*Escherichia coli* Braun lipoprotein induces a lipopolysaccharide-like endotoxic response from primary human endothelial cells," J Immunol., 2001, vol. 167, No. 9, pp. 5231-5239.
Opal, "The host response to endotoxin, antilipopolysaccharide strategies, and the management of severe sepsis", Int. J. Med. Microbiol. 2007, 297(5) pp. 365-377.
Park et al., "Outer Membrane Vesicles Derived from *Escherichia coli* Induce Systemic Inflammatory Response Syndrome", PLOS ONE, 2010, vol. 5, No. 6.
Patrick et al., "A comparison of the haemagglutinating and enzymic activities of *Bacteroides fragilis* whole cells and outer membrane vesicles.", Microbial Pathogenesis, 1996, vol. 20, No. 4, pp. 196-202.
Rolhion et al., "Strong decrease in invasive ability and outer membrane vesicle release in Crohn's disease-associated adherent-invasive *Escherichia coli* strain LF82 with the yfgL gene deleted", Journal of Bacteriology, 2005, vol. 187, No. 7, pp. 2286-2296.
Schild et al., "Characterization of *Vibrio cholera* Outer Membrane Vesicles as a Candidate Vaccine for Cholera", Infection and Immunity, 2008, vol. 77, No. 1, pp. 472-484.
Schild et al., "Immunization with *Vibrio* 1-4 *cholerae* Outer Membrane Vesicles Induces Protective Immunity in Mice", Infection and Immunity, 2008, vol. 76, No. 10, pp. 4554-4563.
Yang, et al., "Effects of endotoxin derived from *Escherichia coli* lipopolysaccharide on the pharmacokinetics of drugs," Arch Pharm Res., 2008, vol. 31, No. 9, pp. 1073-1086.
Schmolz, "Autospecificity in *Escherichia coli* autovaccines: Effects on the human immune system in vitro", Old Herborn University Seminar Monograph, 2002, vol. 15, pp. 159-173.
Shen et al., "Outer Membrane Vesicles of a Human Commensal Mediate Immune Regulation and Disease Protection", Cell Host & Microbe, 2012, vol. 12, No. 4, pp. 509-520.
Soderblom, et al., "Effects of the *Escherichia coli* toxin cytolysin A on mucosal immunostimulation via epithelial $Ca^{2+}$ signaling and Toll-like receptor 4", Cell Microbiol., 2005, vol. 7, No. 6, pp. 779-788.
Yadav et al. "A fraction from *Excherichia coli* with anti-*Aspergillus* properties", Journal of Medical Microbiology, 2005, 54:375-379.
Yan, et al., "The Study for the immune-protection of *E. coli* 0157:H7 outer membrane protein in rats", Zhonghua Yixue Zazhi, 2004, vol. 84, No. 1, pp. 58-62.
Serushago et al., "Role of Antibodies against Outer-membrane Proteins in Murine Resistance to Infection with Encapsulated *Klebsiella pneumoniae*", Journal of General Microbiology, 1989, vol. 135, pp. 2259-2268, 1989.
Yadav et al., "Lipopolysaccharide-Mediated Protection against *Klebsiella pneumoniae*-Induced Lobar Pneumonia: Intranasal vs. Intramuscular Route of Immunization", Folia Microbiol, 2004, vol. 50 (1), pp. 83-86.

\* cited by examiner

Scale bar = 100 nm

Scale bar = 100 nm

Scale bar = 1um

Scale bar = 1um a  b

Scale bar = 100 nm    Scale bar = 100 nm average 28.3 nm

Scale bar = 1um    Scale bar = 1um    Scale bar = 100 nm a    b

Scale bar = 100 nm    Scale bar = 100 nm average 34 nm

Scale bar = 200nm    Scale bar = 100 nm average 30 nm

240x

EV + polyI:C

EXTRACELLULAR VESICLES DERIVED FROM GRAM-POSITIVE BACTERIA, AND USE THEREOF

RELATED APPLICATIONS

This application is the U.S. National Phase of International Application No. PCT/KR2010/005721, filed Aug. 26, 2010, which claims the benefit of both Korean Patent Application No. 10-2009-0083621, filed Sep. 4, 2009 and International Application No. PCT/KR2010/001787, filed Mar. 23, 2010. This application is also a Continuation-in-part application of U.S. patent application Ser. No. 13/393,808, filed Mar. 1, 2012, which is the U.S. National Phase of International Application No. PCT/KR2010/004747, filed Jul. 20, 2010, which claims the benefit of Korean Patent Application No. 10-2009-0082220, filed Sep. 1, 2009.

TECHNICAL FIELD

The present invention relates to Gram-positive bacteria-derived extracellular vesicle (EV), and the uses thereof in a disease animal model, a method for screening a drug candidate, a vaccine, and a method for diagnosing a pathogenic factor of a disease.

BACKGROUND ART

Gram-positive bacteria are those that are stained violet by Gram staining, and lack an outer membrane unlike Gram-negative bacteria. In phylogeny, Gram-positive bacteria belong to the phyla Firmicutes, Actinobacteria, and Tenericutes. Both Firmicutes and Actinobacteria are characterized by the high amount of peptidoglycan in their cell walls. The former, Firmicutes, are low G+C Gram-positive bacteria whereas the latter, Actinobaceria, are high G+C content Gram-positive bacteria. The phylum Tenericutes lacks a cell wall.

Most pathogens in humans are known as Gram-positive bacteria. Representative among them are *Streptococcus* and *Staphylococcus*, both cocci (sphere-shaped bacteria). Other Gram-positive pathogens are bacilli (rod-shaped bacteria) and can be subdivided based on their ability to form spores. The non-spore formers are *Corynebacterium* and *Listeria*, whereas *Bacillus* and *Clostridium* produce spores.

Recently, increasing attention has been drawn to the correlation between extracellular vesicles released from Gram-negative bacteria and diseases caused by Gram-negative bacteria [Kuehn, M. J., Kesty, N. C., Bacterial outer membrane vesicles and the host-pathogen interaction. Genes Dev. 2005, 19, 2645-2655]. Gram-negative bacteria-derived extracellular vesicles are known to bud off from the outer membrane. Because Gram-positive bacteria lack the outer membrane, with the plasma membrane enclosed by the cell wall, little has been known about the release of extracellular vesicles from Gram-positive bacteria as well as about the pathogenicity of Gram-positive bacteria-derived extracellular vesicles.

DISCLOSURE

Technical Problem

It is an object of the present invention to provide Gram-positive bacteria-derived extracellular vesicles.

It is another object of the present invention to provide a method for preparing extracellular vesicles from Gram-positive bacteria.

It is a further object of the present invention to provide a disease animal model, constructed by administering Gram-positive bacteria-derived extracellular vesicles to a test animal.

It is still a further object of the present invention to provide a method for screening a drug candidate preventive or therapeutic of a disease, using a disease animal model or an ex vivo screening system.

It is still another object of the present invention to provide a vaccine for the prophylaxis or therapy of a Gram-positive bacteria-derived extracellular vesicle-caused disease, comprising Gram-positive bacteria-derived extracellular vesicles.

It is yet another object of the present invention to provide a vaccine for the prophylaxis or therapy of Gram-positive bacterial infection using Gram-positive bacteria-derived extracellular vesicles.

It is yet a further object of the present invention to provide a method for determining a pathogenic factor of Gram-positive bacteria, using the separated extracellular vesicles.

The objects of the present invention are not limited to those mentioned above, and other objects, advantages and features of the present invention will be clearly understood to those skilled in the art from the following description.

Technical Solution

In accordance with a first aspect thereof, the present invention provides Gram-positive bacteria-derived extracellular vesicles.

In one embodiment of this aspect, the Gram-positive bacteria include bacteria belonging to the phylum Firmicutes, but are not limited thereto.

The phylum Firmicutes includes, but is not limited to, *Staphylococcus*, *Streptococcus*, *Enterococcus*, *Bacillus*, *Corynebacterium*, *Norcardia*, *Clostridium*, *Lactobacillus* and *Listeria*.

According to another embodiment, the Gram-positive bacteria include bacteria belonging to the class Mollicutes, but are not limited thereto.

The class Mollicutes includes, but is not limited to, *Mycoplasma*.

In another embodiment of the aspect, the Gram-positive bacteria comprise *Staphylococcus aureus*, *Staphylococcus epidermidis*, and *Bacillus subtilis*.

In another embodiment, the Gram-positive bacteria-derived extracellular vesicles include, but are not limited to, those secreted from the Gram-positive bacteria that live within an animal. The extracellular vesicles can be isolated from an internal body secretions from animals. The secretions include skin lavage fluid, snivel, phlegm, feces, blood, urine, synovial, cerebrospinal fluid, pleural fluid, and ascites.

In another embodiment, Gram-positive bacteria-derived extracellular vesicles include secretions from Gram-positive bacteria that live in the surrounding environment. The surrounding environment includes indoor air, outdoor air, soil, and the sea.

In another embodiment, the Gram-positive bacteria-derived extracellular vesicles may be isolated from a culture of Gram-positive bacteria, but is not limited thereto.

According to another embodiment, the extracellular vesicles are ones that form spontaneously or are artificially formed.

Contemplated in accordance with another aspect of the present invention is a method for preparing Gram-positive bacteria-derived extracellular vesicles.

In one embodiment of this aspect, the method comprises centrifuging a culture of Gram-positive bacteria to give a supernatant; and filtering the supernatant.

In another embodiment, the method comprises the following steps of: centrifuging a culture of Gram-positive bacteria to give a supernatant; filtering the supernatant through a first filter to give a first filtrate; filtering the filtrate through a second filter to give a second filtrate; and ultra-centrifuging the second filtrate to yield Gram-positive bacteria-derived extracellular vesicles as a pellet.

In another embodiment, the method may further comprise concentrating the first filtrate after filtration through the first filter.

In another embodiment, the method may further comprise suspending the pellet subsequent to suspension.

Also contemplated in accordance with a further aspect of the present invention is a disease animal model constructed with Gram-positive bacteria-derived extracellular vesicles.

In this context, the Gram-positive bacteria and the extracellular vesicles are as described respectively above.

In another embodiment, the disease may be a localized disease including, but not limited to, a dermal disease such as atopy, a respiratory disease, such as rhinitis, sinusitis, nasopharyngeal cancer, bronchitis, asthma, chronic obstructive pulmonary disease, bronchiectasis, pneumonia, and lung cancer, a digestive disease such as stomatitis, oral cavity cancer, esophagitis, esophageal cancer, gastritis, stomach cancer, inflammatory bowel disease, and colorectal cancer, and a genital disease such as vaginitis, cervicitis, and uterine cervical cancer.

In another embodiment, the disease may be a systemic disease including, but not limited to, a vascular disease such as sepsis, thrombosis/embolism, arteriosclerosis, stroke, acute coronary syndrome, and ischemic vascular disease, a metabolic disease such as diabetes and obesity, a pulmonary disease such as emphysema, and acute respiratory distress syndrome, a bone disease such as arthritis and osteoporosis, and a cranial nerve disease such as dementia, neurodegenerative diseases, and depression.

In another embodiment, the animal may be a mouse, but is not limited thereto.

In accordance with still a further aspect thereof, the present invention provides a method for establishing a disease animal model, comprising administering Gram-positive bacteria-derived extracellular vesicles to an animal.

In the regard, the Gram-positive bacteria, the extracellular vesicles, and the disease are as described respectively above.

The administration includes transdermal, intranasal, intratracheal, oral, subcutaneous, intraperitoneal, intravascular, and rectal administration.

In accordance with still another aspect thereof, the present invention provides a method for discovering a biomarker, using a disease animal model established with the Gram-positive bacteria-derived extracellular vesicles.

In accordance with yet a further aspect thereof, the present invention provides a method for screening a drug candidate preventive or therapeutic of a disease caused by Gram-positive bacteria-derived extracellular vesicles.

In this regard, the Gram-positive bacteria, the extracellular vesicles, and the disease are as described respectively above.

According to one embodiment of this aspect, the screening method comprises treating cells with the Gram-positive bacteria-derived extracellular vesicles. The cells may include inflammatory cells, epithelial cells, vascular endothelial cells, fibroblast cells, and stem cells. The inflammatory cells include monocytes, neutrophils, eosinophils, basophils, and cells differentiated from monocytes in tissues. The stem cells may be derived from, but not limited to, bone marrow or adipose tissue.

In another embodiment, the screening method may comprise administering a candidate, together with Gram-positive bacteria-derived extracellular vesicles, and determining the level of an inflammation-related mediator or evaluating an inflammation-related signaling pathway.

In accordance with yet another aspect thereof, the present invention provides a vaccine for the prophylaxis or therapy of Gram-positive bacterial infection, comprising Gram-positive bacteria-derived extracellular vesicles.

In this context, Gram-positive bacteria and Gram-positive bacteria-derived extracellular vesicles are as described above, respectively.

According to one embodiment of this aspect, the Gram-positive bacterial infection may include, but is not limited to, skin infection, respiratory infection, urogenital infection, bone infection, central nervous system infection, and sepsis.

According to another embodiment of this aspect, the vaccine may be modified to enhance medicinal efficacy or alleviate side effects. The modification may be achieved by the use of transformed bacteria or by the treatment of bacteria with a compound. This compound may include a drug.

In another embodiment, the extracellular vesicles may be modified by treatment with a compound so as to enhance medicinal efficacy or alleviate side effects, said compound including a drug.

In a further embodiment, the vaccine may be used in combination with a drug or an immunostimulant to enhance medicinal efficacy or alleviate side effects, but the present invention is not limited by this.

In accordance with still yet a further aspect thereof, the present invention provides a vaccine preventive or therapeutic against a disease caused by Gram-positive bacteria-derived extracellular vesicles, comprising Gram-positive bacteria-derived extracellular vesicles.

In this connection, the Gram-positive bacteria, the extracellular vesicles, and the disease are as mentioned above, respectively.

According to another embodiment, the vaccine may be modified to enhance medicinal efficacy or alleviate side effects. The modification may be achieved by the use of transformed bacteria or by the treatment of bacteria with a compound. This compound may include a drug.

In another embodiment, the extracellular vesicles may be modified by treatment with a compound so as to enhance medicinal efficacy or alleviate side effects, said compound including a drug.

In a further embodiment, the vaccine may be used in combination with a drug or an immunostimulant to enhance medicinal efficacy or alleviate side effects, but the present invention is not limited by this.

Contemplated in accordance with still yet another aspect of the present invention is a method for preventing or treating a disease which comprises administering Gram-positive bacteria-derived extracellular vesicles at a sub-lethal dose to a mammal.

In this context, the Gram-positive bacteria and the Gram-positive bacteria-derived extracellular vesicles are as described above.

According to one embodiment of this aspect, the disease includes a disease that is caused or aggravated by Gram-positive bacteria-derived extracellular vesicles.

In another embodiment, the disease may be a localized disease including, but not limited to, a thermal disease such as atopy, a respiratory disease, such as rhinitis, sinusitis, nasopharyngeal cancer, bronchitis, asthma, chronic obstructive pulmonary disease, bronchiectasis, pneumonia, and lung cancer, a digestive disease such as stomatitis, oral cavity cancer, esophagitis, esophageal cancer, gastritis, stomach cancer, inflammatory bowel disease, and colorectal cancer, and a genital disease such as vaginitis, cervicitis, and uterine cervical cancer.

In another embodiment, the disease caused or aggravated by gram-positive bacteria-derived extracellular vesicles may be a systemic disease including, but not limited to, a vascular disease such as sepsis, thrombosis/embolism, arteriosclerosis, stroke, acute coronary syndrome, and ischemic vascular disease, a metabolic disease such as diabetes and obesity, a pulmonary disease such as emphysema, and acute respiratory distress syndrome, a bone disease such as arthritis and osteoporosis, and a cranial nerve disease such as dementia, neurodegenerative diseases, and depression.

According to a further embodiment, the disease includes Gram-positive bacterial infections.

The Gram-positive bacterial infections of the present invention may include skin infections, respiratory infections, urogenital infections, bone infections, central nervous system infections and sepsis, but are not limited thereto.

In another embodiment, the administration includes subcutaneous injection, dermal application, intravenous injection, intranasal administration, sublingual administration, intratracheal inhalation, oral administration, and intrarectal administration.

In another embodiment, the extracellular vesicles may be modified to enhance medicinal efficacy or alleviate side effects. The modification may be achieved by the use of transformed bacteria or the treatment of bacteria or extracellular vesicles with a compound. This compound may include a drug.

In a further embodiment, the extracellular vesicles may be used in combination with a drug or an immunostimulant to enhance medicinal efficacy or alleviate side effects, but the present invention is not limited to this.

Also, contemplated in accordance with an additional aspect of the present invention is a method for diagnosing a factor causative of a disease through the application of Gram-positive bacteria-derived extracellular vesicles.

In this context, the Gram-positive bacteria and the extracellular vesicles are as described above, respectively.

In one embodiment of this aspect, the disease includes a disease that is caused or aggravated by Gram-positive bacteria-derived extracellular vesicles. The disease caused or aggravated by Gram-positive bacteria-derived extracellular vesicles is as mentioned above.

According to another embodiment, the disease includes Gram-positive bacterial infections. The Gram-positive bacterial infections of the present invention may include skin infections, respiratory infections, urogenital infections, bone infections, central nervous system infections and sepsis, but are not limited thereto.

According to another embodiment, the application may comprise analyzing the base sequences of a genetic material contained in the Gram-positive bacteria-derived extracellular vesicles. The genetic material may be 16S rRNA, but is not limited thereto.

According to another embodiment, the application may include the determination of the level of proteins in the Gram-positive bacteria-derived extracellular vesicles or the determination of an immune response to the Gram-positive bacteria-derived extracellular vesicles, but is not limited thereto. The determination of an immune responses may include the quantitative determination of antibodies to the Gram-positive bacteria-derived extracellular vesicles, but is not limited thereto.

In another embodiment, the diagnosis may be determined with a sample selected from the group consisting of, but not limited to, blood, phlegm, snivel, feces, urine, cerebrospinal fluid, synovial fluid, pleural fluid, and ascites.

Advantageous Effects

Based on the finding that extracellular vesicles derived from *Staphylococcus aureus*, a Gram-positive bacterium that colonizes the digestive tract or lives in surrounding environments, cause local diseases characterized by dermal and mucosal inflammation, as well as systemic disease, such as sepsis, characterized by systemic inflammatory responses upon introduction into blood, and intravascular coagulation-induced thrombosis/embolism, the present invention utilizes Gram-positive bacteria-derived extracellular vesicles in establishing a disease model, a method for screening drug candidates preventive or therapeutic of diseases, a vaccine for the prophylaxis or therapy of diseases, and a method for the diagnosis of a pathogenic factor of a disease.

In the present invention, it was found that, when Gram-positive bacteria-derived extracellular vesicles were applied to cells, they induced the secretion of an inflammatory factor from the cells and, when administered topically, caused dermal or mucosal inflammation, and systemic diseases including sepsis, intravascular blood coagulation-induced thrombosis/embolism when intraperitoneally injected. Thus, the present invention may be utilized to construct a disease animal model and a method for effectively screening drug candidates. In addition, the disease model or screening method using Gram-positive bacteria-derived extracellular vesicles allows the effective excavation of drugs preventive or therapeutic of diseases caused by the Gram-positive bacteria-derived extracellular vesicles. Further, Gram-positive bacteria-derived extracellular vesicles or their modifications can be applied to the development of a vaccine preventive or therapeutic of Gram-positive bacterial infections or a disease caused by the Gram-positive bacteria-derived extracellular vesicles because they can induce controlled immune responses when they are administered. Moreover, Gram-positive bacteria-derived extracellular vesicles are also utilized to develop a technology used to diagnose a pathogenic factor of Gram-positive bacterial infections or the diseases caused by the Gram positive bacteria-derived extracellular vesicles.

BEST MODE

Figure 1:
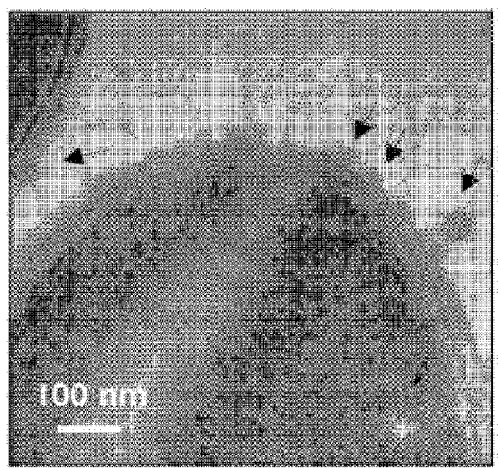
FIG. 1 is of transmission electron microscope images showing *Staphylococcus aureus* from which extracellular vesicles bud off.
Figure 1:
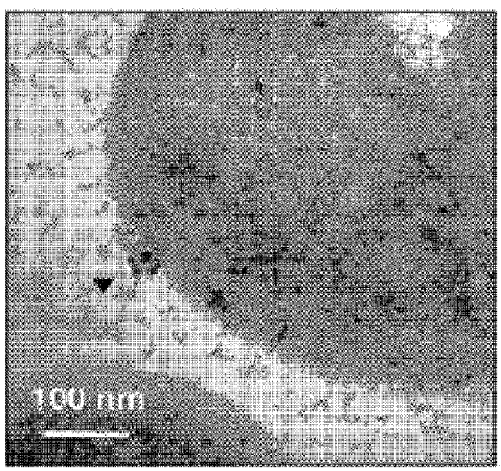

As used herein, the term "Gram-positive bacteria" is intended to encompass those that belong to the phylum Firmicutes and the phylum Actinobacteria, both characterized by the lack of the outer membrane and the presence of a thick cell wall, and the class Mollicutes that lacks cell walls and cannot be Gram-stained, but appear to have derived evolutionarily from the phylum Firmicutes. Among the Gram-positive bacteria with the cell wall are *Staphylococcus, Streptococcus, Enterococcus, Bacillus, Croynebacterium, Norcardia, Clostridium, Lactobacillus, Actinobacteria,* and *Listeria. Mycoplasma* is representative of cell wall-devoid Gram-positive bacteria.

As used herein the term "internal body" is intended to encompass the skin surfaces and the lumens and linings of internal tubular structures in animals. By the term "internal tubular structures" are meant those related to the tracts including the digestive tract, the respiratory tract and the urogenital tract. For example, "digestive tract" includes the oral cavity, the gullet, the stomach, the small intestine, the large intestine, the rectum, the anus, the bile duct, the cystic duct, and the pancreatic duct. The "respiratory tract" includes the conjunctiva, the nasal cavity, the paranasal sinus, the nasopharynx, the trachea, the bronchus, the bronchiole, and the alveolus. The "urogenital tract" includes the kidney, the ureter, the bladder, the urethra, the vagina, the uterine cervix, and the uterus. However, the present invention is not limited by these examples.

By the term "surrounding environment" is meant all environments but the internal body, including, but not limited to, indoor air, outdoor air, soil and the sea.

The term "Gram-positive bacteria-derived extracellular vesicles," as used herein, refers to ones that form spontaneously or are artificially secreted by Gram-positive bacteria that live in the internal body. Typically, vesicles are smaller in size than their source cells, but this does not limit the scope of the present invention in any way.

Gram-positive bacteria refer to bacteria that are stained violet by Gram staining, and lack the outer membrane and contain high amounts of peptidoglycan in their cell walls as opposed to Gram-negative bacteria.

Phylogenetically, Gram-positive bacteria are classified into the phylum Firmicutes, characterized by a thick cell wall and low G+C content, which may be sphere-shaped (cocci) such as in *Staphylococcus, Streptococcus* and *Enterococcus*, or rod-shaped (bacilli) such as in *Bacillus, Corynebacterium, Nocardia, Clostridium, Lactobacillus, Listeria*.

The class Mollicutes, although lacking the cell wall, appears to have derived evolutionarily from the phylum Firmicutes and thus is classified as Gram-positive bacteria. Typical is *Mycoplasma*.

Most pathogens in humans are Gram-positive bacteria. Representative among them are *Streptococcus, Staphylococcus, Corynebacterium, Listeria, Bacillus* and *Clostridium*.

In the 1960s, electron microscopy revealed that Gram-negative cells release extracellular vesicles. Extracellular vesicles released from Gram-negative bacteria are spherical with a size of 20-200 nm and consist of phospholipid bilayers. Gram-negative bacterial extracellular vesicles have various outer membrane proteins as well as LPS. Recently, the present inventors first reported that gut flora-derived extracellular vesicles, when systemically absorbed into the body, cause systemic diseases such as sepsis, blood coagulation, emphysema, etc.

The prejudicial knowledge that extracellular vesicles are released mostly from the outer membrane as in Gram-negative bacteria have blocked the discovery of the extracellular vesicles released from Gram-positive bacteria because Gram-positive bacteria lack the outer membrane and are enclosed by a thick cell wall.

In the present invention, it was first reported that the coccal Gram-positive bacteria *Staphylococcus aureus* and *Staphylococcus epidermidis* release extracellular vesicles that are found to be spherical on an electron microscope and to range in size from 10 to 100 nm as measured by a dynamic light scattering method.

Also, the present inventors first reported the extracellular vesicles derived from the rod-shaped Gram-positive bacteria *Bacillus subtilis* which are observed to be spherical on an electron microscope, with a size of 10~100 nm measured by a dynamic light scattering method.

In the present invention, proteomic analysis was performed on *Staphylococcus aureus*-derived extracellular vesicles through in-gel tryptic digestion and in-solution tryptic digestion, which resulted in the identification of 41 and 84 proteins, respectively. Of them, 35 proteins were overlapped between the two tryptic digestions, so that a total of 90 proteins were detected from *Staphylococcus aureus*-derived extracellular vesicles.

A variety of proteins associated with diseases were identified from *Staphylococcus aureus*-derived extracellular vesicles. The superantigens *staphylococcus* enterotoxin Q and *staphylococcus* secretory antigens (ssaA1, ssaA2) that act as virulent proteins responsible for the onset of sepsis or toxic shock syndrome exist in the *Staphylococcus aureus*-derived extracellular vesicles. Also contained in the vesicles are toxins, such as alpha-hemolysin and gamma-hemolysin, which destroy erythrocytes and degrade hemoglobin. The proteases staphopain A and extracellular ECM and plasma binding protein, which are directly involved in the invasion and penetration of bacteria into host tissues, were also found in the vesicles. Also, blood coagulation-related proteins such as staphylocoagulase, and von Willebrand factor-binding proteins were identified. These proteins are implicated in the onset of sepsis and toxic shock syndrome, characterized by intravascular blood coagulation, as well as vascular diseases including acute coronary syndrome and stroke, caused by thrombus formation within a coronary artery, deep vein thrombosis and pulmonary embolism. Also found in the extracellular vesicles are *S. aureus* IgG-binding protein (SbI) that can endow the bacteria with the function of immune evasion by inhibiting the phagocytosis of host immune cells that is implicated in the onset of atopic dermatitis by inducing the expression of IL-18 in epidermal cells and increasing serum IgE levels.

On the basis of the presence of proteins responsible for various diseases in *Staphylococcus aureus*-derived extracellular vesicles as identified by proteomic analysis, *Staphylococcus aureus*-derived extracellular vesicles were administered ex vivo to mouse macrophages to examine the secretion of inflammatory cytokines. *Staphylococcus aureus*-derived extracellular vesicles induced the secretion of the inflammatory cytokines TNF-$\alpha$ and interleukin-6 (IL-6) in a dose-dependent manner.

The ability of *Staphylococcus aureus*-derived extracellular vesicles to induce the secretion of inflammatory mediators was also examined in mouse fibroblast cells. Thymic stromal lymphopoietin (TSLP), eotaxin and macrophage inflammatory protein (MIP)-1$\alpha$ as well as TNF (tumor necrosis factor)-$\alpha$ and IL-6 were secreted from the fibroblast cells treated with *Staphylococcus aureus*-derived extracellular vesicles.

*Staphylococcus aureus* lives on the skin and almost 100% particularly on the skin of atopic dermatitis patients. A dermal test was conducted to examine whether *Staphylococcus aureus*-derived extracellular vesicles cause local inflammation such as atopic dermatitis. An inflammation such as in atopic dermatitis patients was observed when *Staphylococcus aureus*-derived extracellular vesicles were applied three times a week for 4 weeks to make observations following tape stripping. In addition, extracellular vesicles isolated from the skin lavage fluid of atopic dermatitis patients were found to originate from *Staphylococcus aureus* as measured by a *Staphylococcus aureus*-derived extracellular vesicle-specific antibody. Further, sera of atopic dermatitis patients contained a significantly higher level of *Staphylococcus aureus*-derived extracellular vesicle-specific IgE antibody than did those of normal persons. From these results, it is obvious that *Staphylococcus aureus*-derived extracellular vesicles act as an important factor in the generation or exacerbation of atopic dermatitis.

*Staphylococcus aureus* is transmitted through the air and infects the upper respiratory tract mucosa. In the present invention, an examination was made to see whether *Staphylococcus aureus*-derived extracellular vesicles induces local inflammation on the respiratory tract mucosa. When *Staphylococcus aureus*-derived extracellular vesicles were intranasally administered once, the population of inflammatory cells in bronchoalveolar lavage fluid was increased with an increase in the concentration of the vesicles. The level of IL-6, which plays an important role in the differentiation of Th17 (type 17 helper T), was increased, as well. When *Staphylococcus aureus*-derived extracellular vesicles were intranasally administered twice a week for three weeks, the total count of inflammatory cells, and particularly the neutrophil count were increased in the bronchoalveolar lavage fluid, with the concomitant high production of IL-17 from Th17. These results indicate that *Staphylococcus aureus*-derived extracellular vesicles act as a pathogenic factor of IL-17-mediated neutrophilic inflammation on the mucosa.

Sepsis is characterized by systemic inflammation and the presence of a pathogenic substance in blood after a local bacterial infection. In the present invention, the induction of sepsis by the intravenous injection of *Staphylococcus aureus*-derived extracellular vesicles was examined. Around 40% of the mice intravenously injected with a high dose of the extracellular vesicles were dead. Also, hypothermia, a criterion for sepsis, was observed after the injection of the extracellular vesicles, demonstrating that *Staphylococcus aureus*-derived extracellular vesicles may cause sepsis when introduced into blood vessels.

As identified above in the proteomic analysis, *Staphylococcus aureus*-derived extracellular vesicles contain blood coagulation-related proteins. In the present invention, an examination was made to see whether the *Staphylococcus aureus*-derived extracellular vesicles cause blood coagulation and thus form thrombus. When administered intravenously, subcutaneously, or intranasally, *Staphylococcus aureus*-derived extracellular vesicles elevated the level of D-dimer, an index for intravascular coagulation, in serum and reduced the count of platelets, another index, in peripheral blood. Also, thrombus was observed in pulmonary blood vessels upon the intravenous, subcutaneous or intranasal administration of the *Staphylococcus aureus*-derived extracellular vesicles. These results thus suggest that when introduced into blood vessels, *Staphylococcus aureus*-derived extracellular vesicles may induce thrombosis or embolism through intravascular coagulation.

It is very important to clarify the exact causative factors of a disease to develop drugs for the prevention or treatment thereof. For example, drug candidates can be screened for pharmaceutical efficacy either in the course of the ex vivo treatment of cells with the causative factor or when administered to the animal model. The present invention includes the development of a method for screening drug candidates using *Staphylococcus aureus*-derived extracellular vesicles, and using the method or drugs useful for preventing or treating Gram-positive bacteria-derived extracellular vesicle-caused diseases. For instance, of 102 different prodrugs, the pharmaceutical efficacy of 19 candidate drugs was screened and evaluated in the disease animal model. That is, the screening method according to the present invention can be used to discover drugs preventive or therapeutic of Gram-positive bacteria-derived extracellular vesicles.

In addition, immune adjuvants including lipoteichoic acid (LTA) and peptidoglycans as well as various proteins including toxin proteins (Staphylococcal enterotoxin Q, K) are found in *Staphylococcus aureus*-derived extracellular vesicles. During the course of development of the present invention, immunological markers in mice were analyzed in order to evaluate the utility of using *Staphylococcus aureus*-derived extracellular vesicles as a vaccine for the prophylaxis and therapy of bacterial infections. The present invention also provides a method for enhancing the efficacy of the extracellular vesicles or alleviating the side effects of the extracellular vesicles. When *Staphylococcus aureus*-derived extracellular vesicles were subcutaneously injected, together with the synthetic dsRNA polyinosinic-polycytidylic acid (polyI:C), to mice, blood IgG levels were elevated along with the splenocyte cytokines IFN (interferon)-γ and IL-17. Hence, *Staphylococcus aureus*-derived extracellular vesicles, when subcutaneously injected, can effectively induce Th1 (type 1 helper T cell) and Th17 immune responses as well as antibody reactions.

*Staphylococcus aureus*-derived extracellular vesicles were evaluated for pharmaceutical efficacy as a vaccine against *Staphylococcus aureus*-caused pneumonia. When pneumonia was induced in mice, any of the mice challenged with the vesicle vaccine did not die, whereas about 60% of the non-immunized mice died of pneumonia. This result implies that the *Staphylococcus aureus*-derived extracellular vesicles can be useful as a vaccine that prevents bacterial infections.

As described above, a variety of diseases may be generated by *Staphylococcus*-derived extracellular vesicles, indicating that the extracellular vesicles serve as an important pathogenic agent for the diseases which have remained unclear about their causes. To provide a method for the diagnosis of a pathogenic agent, bacterial extracellular vesicles were examined to see whether they contain a genetic material. As a result, 16S rRNA and DNA were detected as measured by PCR. Based on this observation, the examination of genetic materials in a sample such as blood, which can be easily taken, allows the pathogenic agent of a disease to be readily identified, thus enabling the disease to be diagnosed.

A better understanding of the present invention may be obtained through the following examples which are set forth to illustrate, but are not to be construed as limiting the present invention.

Example 1

Electron Microscopic Observation of *Staphylococcus aureus*

*Staphylococcus aureus* (ATCC14458) was grown to an O.D. at 600 nm of 1 in nutrient broth. After the centrifugation of the broth at 10,000×g for 20 min, the *Staphylococcus aureus* pellet was fixed for 2 hours in 2.5% glutaraldehyde and post-fixed for 1 hour in 1% osmium tetroxide. Dehydration with a series of graded ethanol solution was followed by epoxy resin embedment. The resulting block was sectioned into ultrathin slices 70 nm thick. The cell sections were adsorbed for 3 min onto a glow-discharged carbon-coated copper grid and stained with 2% uranylacetate and lead citrate. Transmission electron microscope (TEM) (JEM101, Jeol, Japan) observations were made of the cell. As can be seen in the TEM images of FIG. 1, extracellular vesicles with a size of 20~100 nm were observed to bud off from *Staphylococcus aureus*.

Likewise, scanning electron microscopy (SEM) was performed. In this regard, the same *Staphylococcus aureus* culture as was mentioned above was centrifuged after which the cell pellet was fixed for 1 hour in 2.5% glutaraldehyde, post-fixed for 1 hour in 1% osmium tetroxide, and dehydrated in a series of graded ethanol solutions before a critical point drying process using a $CO_2$ system (HCP-2 critical point dryer, HITACH, Japan). The bacterial sample was mounted on a stub and coated with platinum (Pt) for observation under a JSM-7401F scanning electron microscope (Jeol, Japan).

Figure 2:
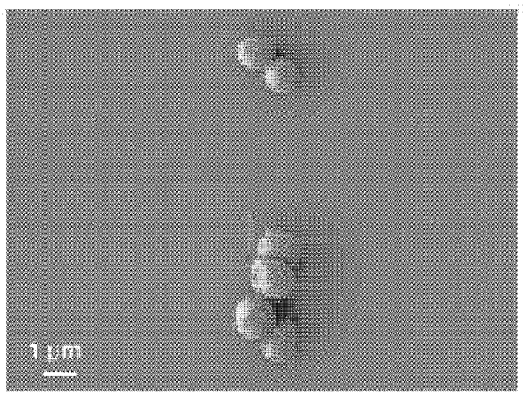
FIG. 2 is of scanning electron microscope images showing *Staphylococcus aureus* from which extracellular vesicles bud off.
Figure 2:
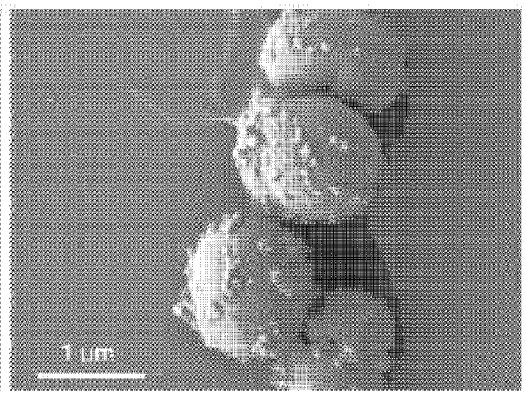

As can be seen in the SEM images of FIG. 2, *Staphylococcus aureus* released extracellular vesicles.

Example 2

Preparation of *Staphylococcus aureus*-Derived Extracellular Vesicles

[General Extracellular Vesicles Isolation]

*Staphylococcus aureus* was inoculated into 3 ml of nutrient broth in a test tube and cultured at 37° C. for 6 hour. Of the culture, 5 μL was transferred to 500 ml of nutrient broth in a 2 L Erlenmeyer flask and incubated at 37° C. for 4 hours to an O.D. (600 nm) of 1.0. All the culture was equally assigned to 500 mL-ultracentrifuge tubes and spun at 4° C. and 10,000×g for 20 min. The supernatant was allowed to pass once through a membrane filter with a pore size of 0.45 μm, and the filtrate was 25-fold concentrated using the Quixstand system with 100 kDa cutoff. After one passage of the concentrate through a membrane filter with a pore size of 0.22 μm, the resulting filtrate was ultra-centrifuged at 4° C. and 150,000×g for 3 hours in 70 mL-ultracentrifuge tubes. The pellets thus formed were re-suspended in PBS (phosphate buffered saline) to separate extracellular vesicles derived from *Staphylococcus aureus*.

[Isolation of Extracellular Vesicles for Use in Proteomic Analysis]

The same concentrate as was obtained in the general isolation of extracellular vesicles was allowed to pass once through a membrane filter with a pore size of 0.22 μm, followed by ultracentrifugation at 4° C. and 150,000×g for 3 hours in 70 ml-ultracentrifuge tubes. The pellet was suspended in 2.2 mL of 50% Optiprep solution. The suspension was placed in a 5 ml-ultracentrifuge tube, followed by the addition of 2 mL of a 40% Optiprep solution and 0.8 mL of a 10% Optiprep solution to the suspension in that order. Ultracentrifugation at 4° C. and 200,000×g for 2 hours formed a layer of extracellular vesicles between the 40% Optiprep solution and the 10% Optiprep solution.

Example 3

Characteristics of *Staphylococcus aureus*-Derived Extracellular Vesicles

The extracellular vesicles which were isolated from *Staphylococcus aureus* as in Example 2 were adsorbed for 3 min onto a glow-discharged carbon-coated copper grid which was then washed with distilled water and stained with 2% uranylacetate before observation with a JEM101 transmission electron microscope.

Figure 3:
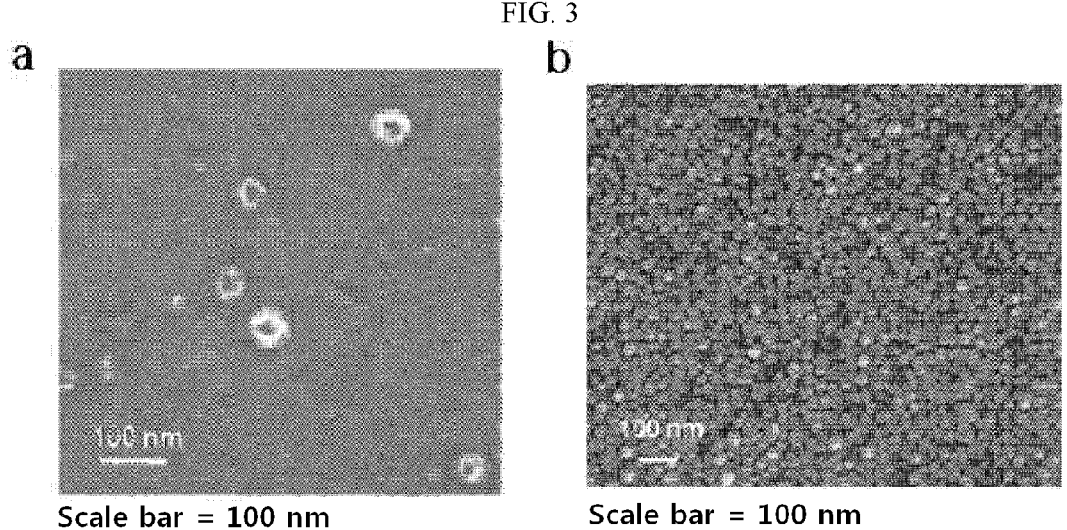
FIG. 3 is a transmission electron microscope image (a) and a scanning electron microscope image (b) showing extracellular vesicles isolated from *Staphylococcus aureus*.

As shown in the TEM image of FIG. 3a, *Staphylococcus aureus*-derived extracellular vesicles are closed spheres with a size of 20-100 nm. The isolated extracellular vesicles were attached onto cover glass, fixed for 1 hour in 2.5% glutaraldehyde, post-fixed for 1 hour in 1% osmium tetroxide, dehydrated in a series of graded ethanol solutions and then subjected to critical point drying using a $CO_2$ system. The extracellular vesicles attached to the cover glass were mounted on the stub and observed with a JSM-7401F scanning electron microscope.

As is understood from the SEM image of FIG. 3b, the extracellular vesicles are spherical with relatively uniform sizes (20-100 nm).

The *Staphylococcus aureus*-derived extracellular vesicles that were isolated as in Example 2 were diluted to 1 µg/ml in 1 mL of PBS. This PBS was placed in a cuvette which was then subjected to particle size analysis using dynamic light scattering. The result is depicted in FIG. 4.

Figure 4:
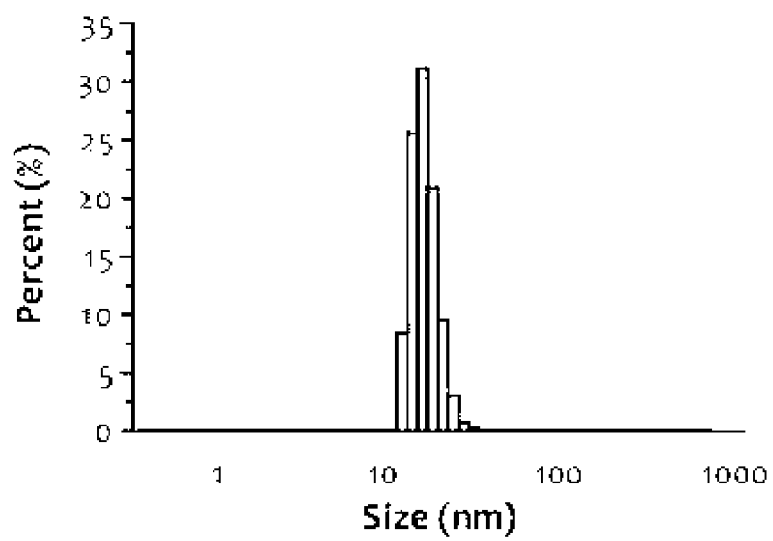
FIG. 4 is a graph showing a size distribution of the extracellular vesicles isolated from *Staphylococcus aureus*.

As shown in FIG. 4, extracellular vesicles range in size from 20 to 100 nm, with a mean particle size of 28.3 nm.

Whole cell proteins, cell wall proteins, membrane proteins and cytosolic proteins were obtained as follows. *Staphylococcus aureus* was grown to an O.D. (600 nm) of 1.0 in 3 ml of nutrient broth, followed by centrifugation at 10,000×g for 20 min. The cell pellet thus formed was incubated with 20 µg/ml lysostaphin buffer (Tris-EDTA) at 37° C. for 15 min. Then, the cells were completely disrupted with sonication and centrifuged at 8000×g for 10 min. The supernatant devoid of insoluble materials was used as a whole cell protein. In order to form a protoplast, separately, the *Staphylococcus aureus* cell pellet was incubated with 20 µg/ml lysostaphin buffer (Tris-EDTA) and 1.1 M sucrose at 37° C. for 15 min. After centrifugation at 10,000×g for 20, the supernatant was used as cell wall proteins. The resulting pellet was resuspended in hypotonic buffer and ultracentrifuged at 40,000×g for 1 hour. The supernatant was used for the cytosolic proteins while the pellet was suspended in Tris buffer (10 mM Tris-HCl, pH 8.0) and used for the membrane proteins. To 7 µg of each of the whole cell protein, the cell wall protein, the cytoplasmic protein and the extracellular vesicle protein isolated in Example 2 was added such an amount of 5× loading dye (250 mM Tris-HCl, 10% SDS, 0.5% bromophenol blue, 50% glycerol) that the loading dye was diluted to 1× before boiling at 100° C. for 10 min. The protein samples were loaded onto 10% polyacrylamide gel and run at 80 V for 2 hours by electrophoresis. The gel was stained for 2 hours with 0.25% Coomassie Brilliant Blue, followed by incubation for 6 hour in a destaining solution (Methanol:DDW:Acetic acid=5:4:1).

Figure 5:
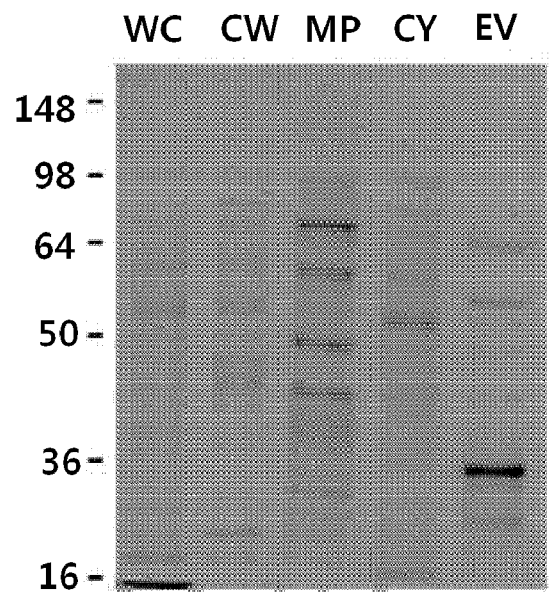
FIG. 5 is a photograph showing SDS-PAGE results of *Staphylococcus* proteins in the whole cell (WC), the cell wall (CW), the plasma membrane (MP) the cytoplasm (CY) and the extracellular vesicles (EV), as stained with Coomassie blue.

FIG. 5 shows distribution patterns of proteins for *Staphylococcus aureus*-derived extracellular vesicles proteins in the whole cell (WC), the cell wall (CW), the plasma membrane (MP) the cytoplasm (CY) and the extracellular vesicles (EV), as stained with Coomassie blue. As can be seen, specific proteins were sorted within the extracellular vesicles (EV).

Example 4

Electron Microscopic Observation of *Staphylococcus epidermis*

Figure 6:
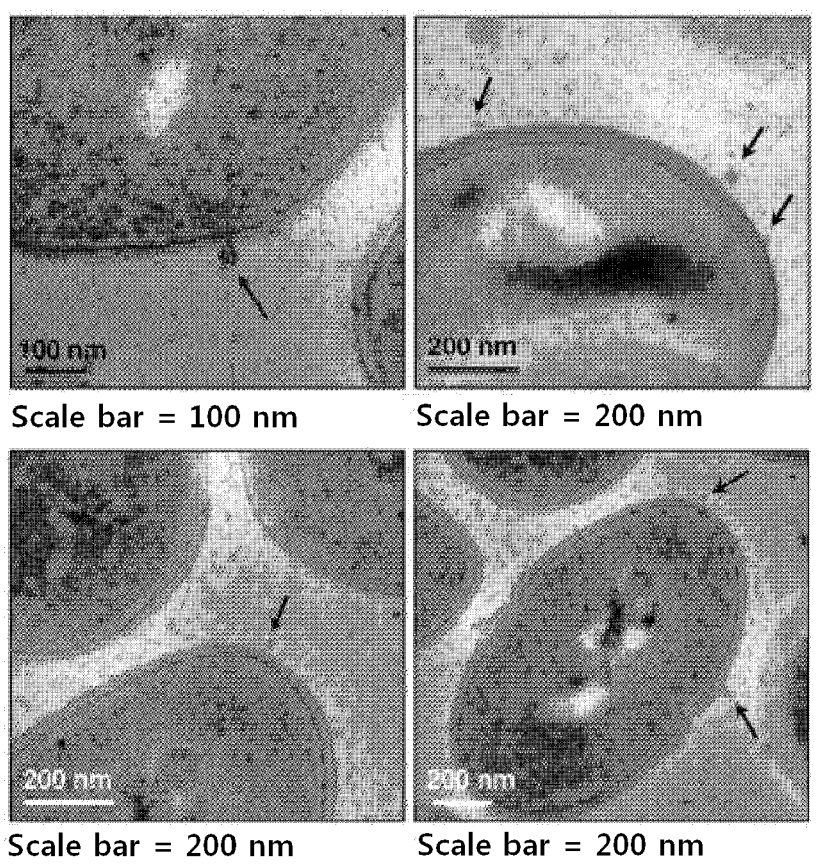
FIG. 6 is of transmission electron microscope images showing *Staphylococcus epidermis* from which extracellular vesicles bud off.

*Staphylococcus epidermis* (ATCC12228) was grown to an O.D. at 600 nm of 1 in nutrient broth. After the centrifugation of the broth at 10,000×g for 20 min, the *Staphylococcus aureus* pellet was fixed for 2 hours in 2.5% glutaraldehyde and post-fixed for 1 hour in 1% osmium tetroxide. Dehydration with a series of graded ethanol solution was followed by epoxy resin embedment. The resulting block was sectioned into ultrathin slices 70 nm thick. The cell sections were adsorbed for 3 min onto a glow-discharged carbon-coated copper grid and stained with 2% uranylacetate and lead citrate. JEM101 transmission electron microscope (Jeol, Japan) observations were made of the cell. As can be seen in the TEM images of FIG. 6, extracellular vesicles with a size of 20~100 nm were observed to bud off from *Staphylococcus epidermis*.

Figure 7:
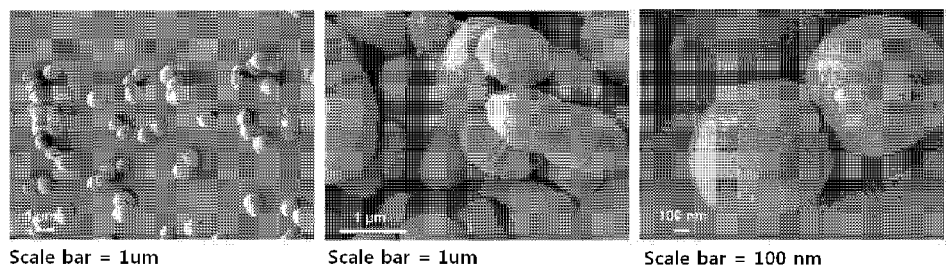
FIG. 7 is of scanning electron microscope images showing *Staphylococcus epidermis* from which extracellular vesicles bud off.

Likewise, scanning electron microscopy (SEM) was performed. In this regard, the same *Staphylococcus epidermis* culture as was mentioned above was centrifuged at 10,000×g for 20 min, after which the cell pellet was fixed for 1 hour in 2.5% glutaraldehyde, post-fixed for 1 hour in 1% osmium tetroxide, and dehydrated in a series of graded ethanol solutions before a critical point drying process using a $CO_2$ system. The bacterial sample was mounted on a stub and coated with platinum for observation under a JSM-7401F scanning electron microscope. As can be seen in the SEM images of FIG. 7, extracellular vesicles budded off from *Staphylococcus epidermis*.

Example 5

Preparation of *Staphylococcus epidermis*-Derived Extracellular Vesicles

*Staphylococcus epidermis* was inoculated into 3 ml of nutrient broth in a test tube and cultured at 37° C. for 6 hour. Of the culture, 5 µL was transferred to 500 ml of nutrient broth in a 2 L-Erlenmeyer flask and incubated at 37° C. for 4 hours to an O.D. (600 nm) of 1.0. All the culture was equally assigned to 500 mL-ultracentrifuge tubes and spun at 4° C. and 10,000×g for 20 min. The supernatant devoid of cells was allowed to pass once through a membrane filter with a pore size of 0.45 µm, and the filtrate was 25-fold concentrated using the Quixstand system with 100 kDa cutoff. After one passage of the concentrate through a membrane filter with a pore size of 0.22 µm, the resulting filtrate was ultra-centrifuged at 4° C. and 150,000×g for 3 hours in 70 mL-ultracentrifuge tubes. The pellets thus formed were re-suspended in PBS to separate extracellular vesicles derived from *Staphylococcus epidermis*.

Example 6

Characteristics of *Staphylococcus epidermis*-Derived Extracellular Vesicles

The extracellular vesicles which were isolated from *Staphylococcus epidermis* as in Example 5 were adsorbed for 3 min onto a glow-discharged carbon-coated copper grid which was then washed with distilled water and stained with 2% uranylacetate before observation with a JEM101 transmission electron microscope.

Figure 8:
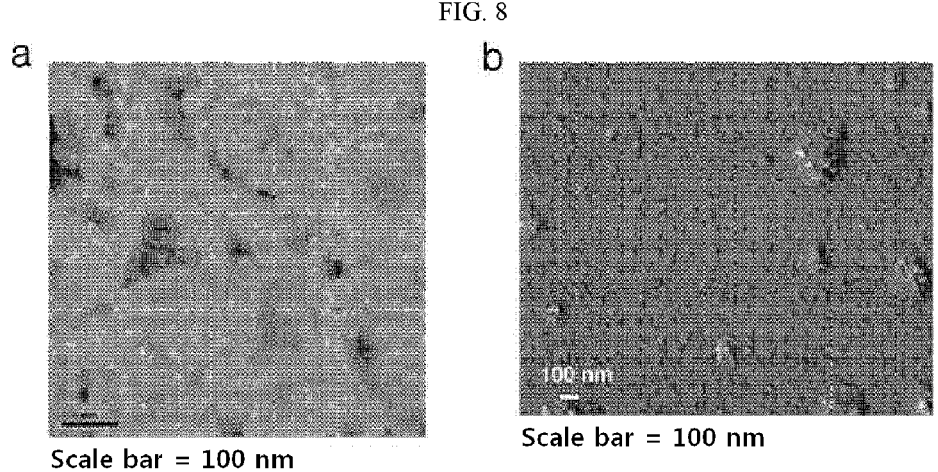
FIG. 8 is a transmission electron microscope image (a) and a scanning electron microscope image (b) showing extracellular vesicles isolated from *Staphylococcus epidermis*.

As shown in the TEM image of FIG. 8a, *Staphylococcus epidermis*-derived extracellular vesicles are closed spheres with a size of 20-100 nm.

The isolated extracellular vesicles were attached onto cover glass, fixed for 1 hour in 2.5% glutaraldehyde, post-fixed for 1 hour in 1% osmium tetroxide, dehydrated in a series of graded ethanol solutions and then subjected to critical point drying using a $CO_2$ system. The extracellular vesicles attached to the cover glass were mounted on the stub and observed with a JSM-7401F scanning electron microscope.

As is understood from the SEM image of FIG. 8b, the extracellular vesicles are spherical with relatively uniform sizes (20-100 nm).

The *Staphylococcus epidermis*-derived extracellular vesicles that were isolated as in Example 2 were diluted to 1 µg/ml in 1 mL of PBS. This PBS was placed in a cuvette which was then subjected to particle size analysis using dynamic light scattering. The result is depicted in FIG. 9.

Figure 9:
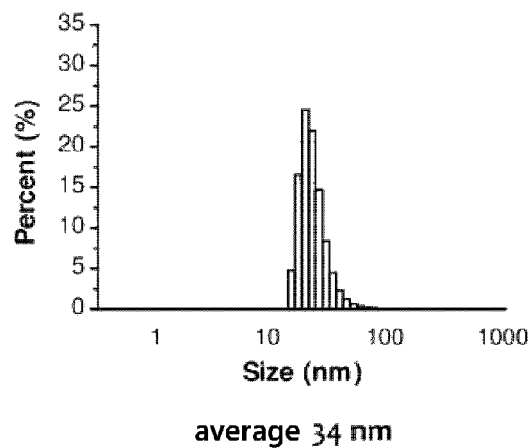
FIG. 9 is a graph showing a size distribution of the extracellular vesicles isolated from *Staphylococcus epidermis*.

As shown in FIG. 9, extracellular vesicles range in size from 20 to 100 nm, with a mean particle size of 34 nm.

Example 7

Electron Microscopic Observation of *Bacillus subtilis*

*Bacillus subtilis* (KCTC3729) was grown to an O.D. at 600 nm of 1 in nutrient broth. After the centrifugation of the broth at 6,000×g for 15 min, the *Bacillus subtilis* pellet was fixed for 2 hours in 2.5% glutaraldehyde and post-fixed for 1 hour in 1% osmium tetroxide. Dehydration with a series of graded ethanol solutions was followed by epoxy resin embedment. The resulting block was sectioned into ultrathin slices 70 nm thick. The cell sections were adsorbed for 3 min onto a glow-discharged carbon-coated copper grid and stained with 2% uranylacetate and lead citrate. JEM101 transmission electron microscope (Jeol, Japan) observations were made of the cell.

Figure 10:
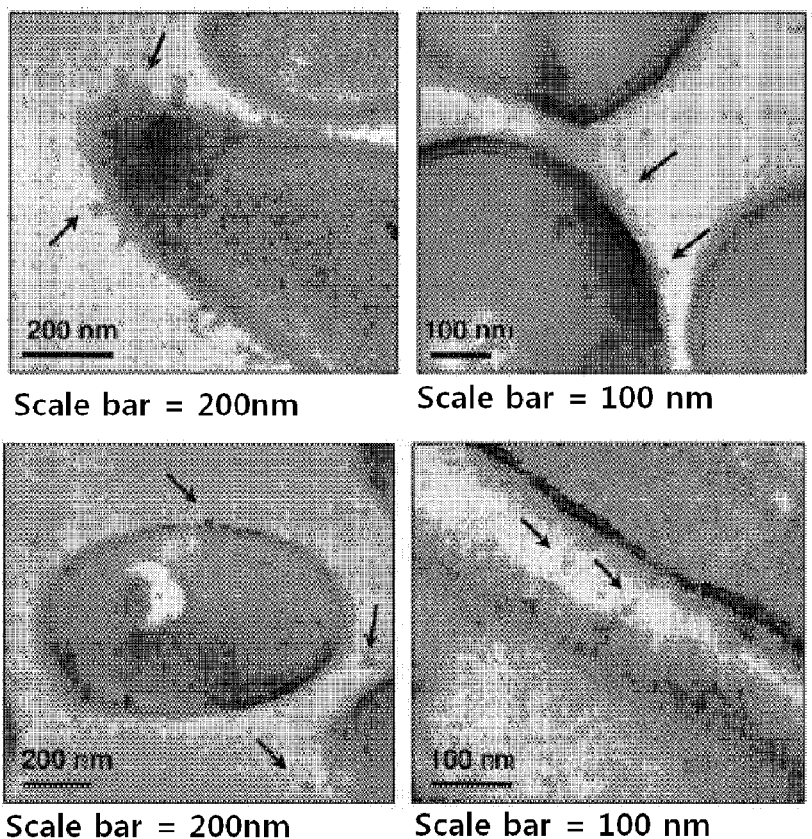
FIG. 10 is of transmission electron microscope images showing *Bacillus subtilis* from which extracellular vesicles bud off.

As can be seen in the TEM images of FIG. 10, extracellular vesicles with a size of 20~100 nm were observed to bud off from *Bacillus subtilis*.

Figure 11:
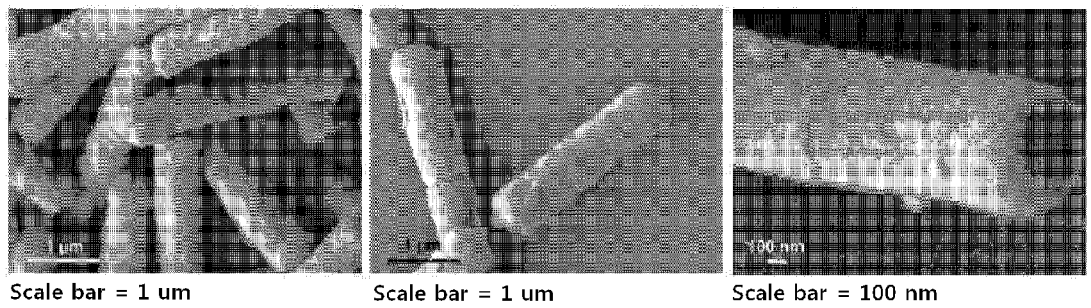
FIG. 11 is of scanning electron microscope images showing *Bacillus subtilis* from which extracellular vesicles bud off.

Likewise, scanning electron microscopy (SEM) was performed. In this regard, the same *Bacillus subtilis* culture as was mentioned above was centrifuged at 6,000×g for 15 min, after which the cell pellet was fixed for 1 hour in 2.5% glutaraldehyde, post-fixed for 1 hour in 1% osmium tetroxide, and dehydrated in a series of graded ethanol solutions before a critical point drying process using a $CO_2$ system. The bacterial sample was mounted on a stub and coated with platinum for observation under a JSM-7401F scanning electron microscope. As can be seen in the SEM images of FIG. 11, extracellular vesicles budded off from *Staphylococcus epidermis*.

Example 8

Preparation of *Bacillus subtilis*-Derived Extracellular Vesicles

*Bacillus subtilis* was inoculated into 3 ml of nutrient broth in a test tube and cultured at 37° C. for 6 hour. Of the culture, 5 µL was transferred to 500 ml of nutrient broth in a 2 L-Erlenmeyer flask and incubated at 37° C. for 4 hours to an O.D. (600 nm) of 1.0. All the culture was equally assigned to 500 mL-ultracentrifuge tubes and spun at 4° C. and 6,000×g for 20 min. The supernatant devoid of cells was allowed to pass once through a membrane filter with a pore size of 0.45 µm, and the filtrate was 25-fold concentrated using the Quixstand system with 100 kDa cutoff. After one passage of the concentrate through a membrane filter with a pore size of 0.22 µm, the resulting filtrate was ultra-centrifuged at 4° C. and 150,000×g for 3 hours in 70 mL-ultracentrifuge tubes. The pellets thus formed were re-suspended in PBS to separate extracellular vesicles derived from *Bacillus subtilis*.

Example 9

Characteristics of *Bacillus subtilis*-Derived Extracellular Vesicles

The extracellular vesicles which were isolated from *Bacillus subtilis* as in Example 8 were adsorbed for 3 min onto a glow-discharged carbon-coated copper grid which was then washed with distilled water and stained with 2% uranylacetate before observation with a JEM101 transmission electron microscope.

Figure 12:
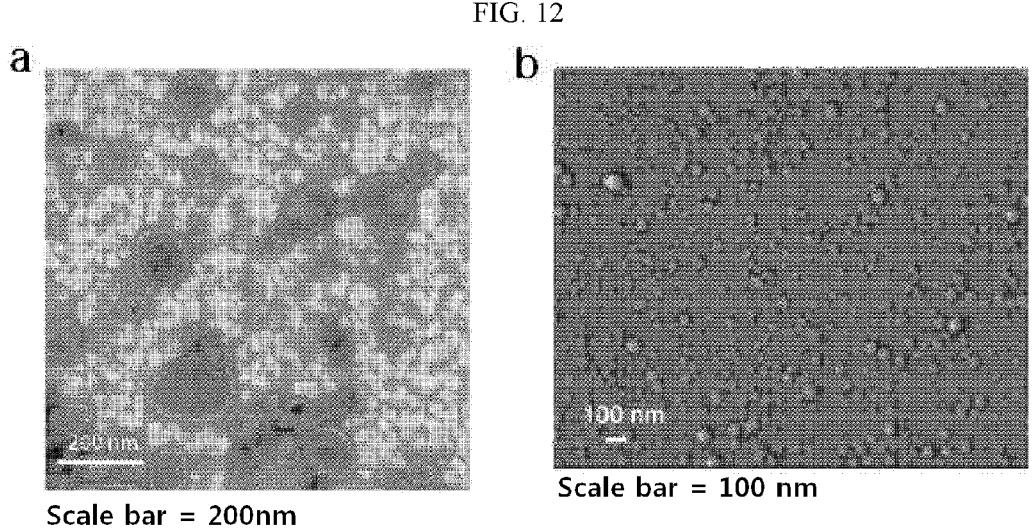
FIG. 12 is a transmission electron microscope image (a) and a scanning electron microscope image (b) showing extracellular vesicles isolated from *Bacillus subtilis*.

As shown in the TEM image of FIG. 12a, *Bacillus subtilis*-derived extracellular vesicles are closed spheres with a size of 20-100 nm.

The isolated extracellular vesicles were attached onto cover glass, fixed for 1 hour in 2.5% glutaraldehyde, post-fixed for 1 hour in 1% osmium tetroxide, dehydrated in a series of graded ethanol solutions and then subjected to critical point drying using a $CO_2$ system. The extracellular vesicles attached to the cover glass were mounted on the stub and observed with a JSM-7401F scanning electron microscope.

As is understood from the SEM image of FIG. 12b, the extracellular vesicles are spherical with relatively uniform sizes (20-100 nm).

The *Bacillus subtilis*-derived extracellular vesicles that were isolated as in Example 8 were diluted to 1 µg/ml in 1 mL of PBS. This PBS was placed in a cuvette which was then subjected to particle size analysis using dynamic light scattering. The result is depicted in FIG. 13.

Figure 13:
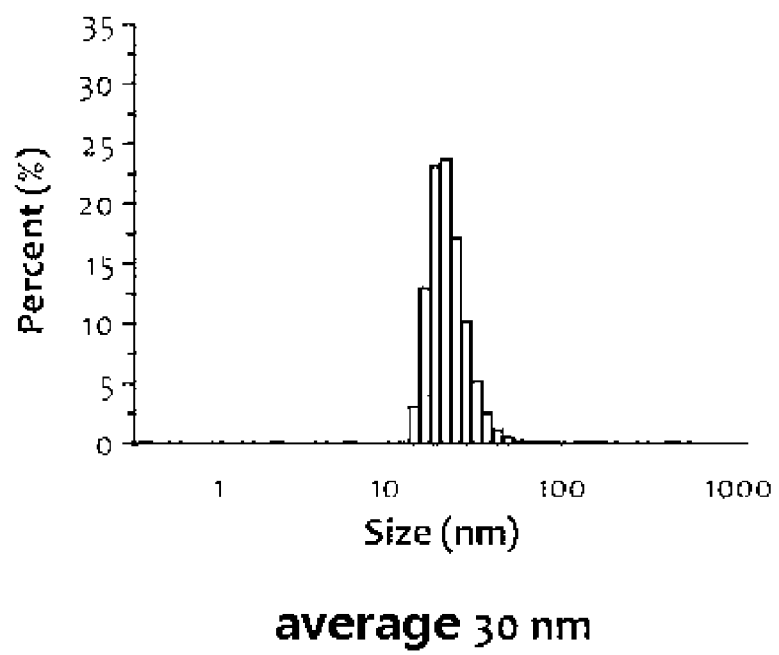
FIG. 13 is a graph showing a size distribution of the extracellular vesicles isolated from *Bacillus subtilis*.

As shown in FIG. 13, extracellular vesicles range in size from 20 to 100 nm, with a mean particle size of 30 nm.

In these Examples, the spontaneous secretion of extracellular vesicles from *Staphylococcus aureus, Staphylococcus epidermis*, and *Bacillus subtilis*, all representative of Gram-positive bacteria, during their growth is first disclosed, along with various characters of isolated extracellular vesicle. However, it should be understood to those skilled in the art that the bacteria which can be used as a source for the extracellular vesicles of the present invention are not limited only to those mentioned in the above Examples, but can be extended to all Gram-positive bacteria. Also, it should be apparent that disease animal models, although established only with *Staphylococcus aureus* in the Examples, can be constructed using any pathogenic Gram-positive bacteria.

Example 10

Proteomic Analysis of *Staphylococcus aureus*-Derived Extracellular Vesicles

[In-Gel Tryptic Digestion]

To 50 µg of the *Staphylococcus aureus*-derived extracellular vesicles isolated for proteomic analysis in Example 2 was added such an amount of 5× loading dye that the loading dye was diluted to 1×, followed by boiling at 100° C. for 10 min. These samples were loaded to 4-20% Novex tris-glycine gel (Invitrogen) and run at 90 V for 2 hours by electrophoresis. After being stained with GelCode Blue Stain Reagent (Pierce), the gel was cut into 11 equal gel pieces which were in turn treated with 13 ng/µL trypsin (Promega) at 37° C. for 16 hour.

[In-Solution Tryptic Digestion]

To 100 µg of the *Staphylococcus aureus*-derived extracellular vesicle sample prepared for proteomic analysis in Example 2 was added four volumes of methanol, followed by spinning at 9000×g for 10 sec. Thereafter, this mixture was mixed with an equal volume of chloroform and spun at 9000×g for 10 sec. HPLC-grade water was added in an amount three times as large as the volume of the sample and spun at 16,000×g for 1.5 min. Of the two separate layers thus formed, the upper layer was removed, while methanol was added in an amount three times as large as the volume of the sample to the remaining layer and centrifuged at 16,000×g for 3 min. The pellet thus formed was suspended in lysis buffer (6 M urea, 40 mM ammonium bicarbonate), followed by reduction by 5 mM tris(2-carbocyethyl)phosphine hydrochloride at room temperature for 1 hour. Then, the sample was incubated with 25 mM iodoacetamide at room temperature for 30 min in a dark condition to alkylate proteins. Finally, the sample was treated with 5 ng/μl trypsin at 37° C. for 16 hours. The peptides thus degraded were separated using the OFFGEL fractionators system (Agilent). To begin with, a 24 cm-long IPG strip (pH 3-10) was hydrated with IPG-rehydration. The degraded peptides were dissolved in 2.8 ml of off-gel buffer, and the solution was loaded in an amount of 150 μl per lane. Electrophoresis at 50 μA, 8000 V for 47 hours separated the peptides according to isoelectric point (pI). The samples were desalted using a PepClean C18 spin column.

[Nano-Ionization Mass Spectrometry (Nano-LC-ESI-MS/MS)]

Mass analysis was done using Nano-LC-ESI-MS/MS. The degraded peptides of *Staphylococcus aureus*-derived extracellular vesicles prepared by the in-gel or in-solution tryptic digestion were loaded to a column (75 μm×12 cm) packed with C18 resin, and then separated as follows: 3-30% buffer, B 70 min; 30-40% buffer B, 5 min; 40-90% buffer B, 20 min; flow rate 0.2 μL/min (buffer A composition: 0.1% formic acid in $H_2O$, buffer B composition: 0.1% formic acid in ACN). The eluted peptides were introduced into an LTQ-ion-trap mass spectrometer (Thermo Finnigan) with a 2.0 kV electrospray voltage under a normalized collision energy set to 35% for MS/MS. All MS/MS spectra were acquired by data-dependent scans in which the five most intense peaks from the full MS scans were selected for fragmentation. The repeat count for dynamic exclusion was set to 1, the repeat duration to 30 sec, and the dynamic exclusion duration to 180 sec, exclusion mass width to ±1.5 Da, and the list size of dynamic exclusion to 50.

[Data Analysis]

One NCBI database was constructed from 9 custom databases containing amino acid and base sequences of *Staphylococcus aureus* by concatenating the target (forward) and decoy (reversed) base sequence combinations. All raw mass spectra were submitted to the SEQUEST engine tool for searches against the NCBI database. Only the proteins for which at least two unique peptides were matched were selected, with the false-positive rates of the identified peptides set to 1%.

[Results]

Figure 14:
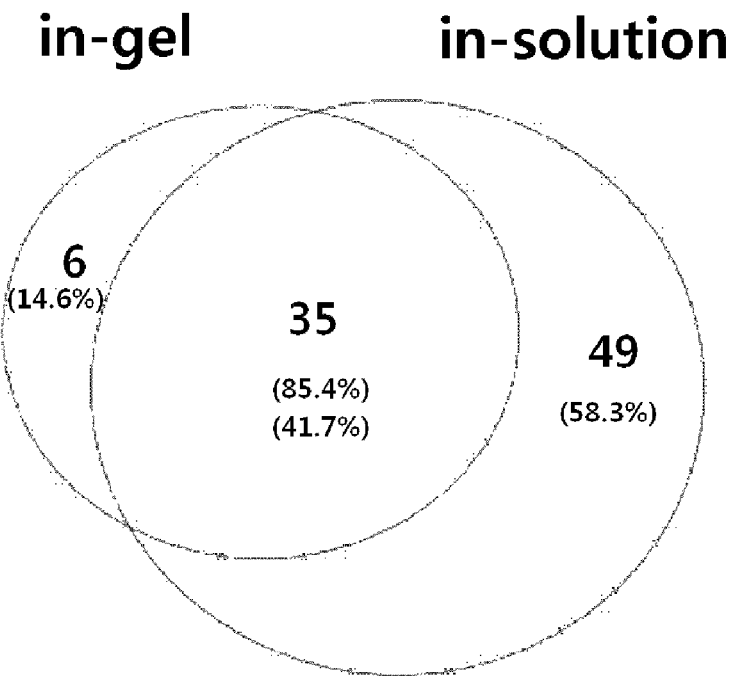
FIG. 14 is a venn diagram showing the identification of 90 proteins of *Staphylococcus aureus*-derived extracellular vesicles by proteomic analysis in which 41 and 84 proteins are detected through in-gel tryptic digestion and in-solution tryptic digestion, respectively, with 35 proteins overlapping between the two tryptic digestions.

The proteomic analysis identified a total of 90 proteins of *Staphylococcus aureus*-derived extracellular vesicles, with 35 overlapped between 41 proteins identified by in-gel tryptic digestion and 84 proteins identified by in-solution tryptic digestion, as shown in FIG. 14. Table 1 summarizes the 90 proteins that were identified.

A variety of disease-related proteins were among the identified extracellular vesicle protein. The superantigens *staphylococcus* enterotoxin Q and *staphylococcus* secretory antigens (ssaA1, ssaA2) that act as virulent proteins responsible for the onset of sepsis or toxic shock syndrome exist in the *Staphylococcus aureus*-derived extracellular vesicles. Also found in the vesicles are toxins, such as alpha-hemolysin and gamma-hemolysin, which destroy erythrocytes and degrade hemoglobin. The proteases staphopain A and extracellular ECM and plasma binding protein, which are directly involved in the invasion and penetration of bacteria into host tissues, were detected in the vesicles. Also, the blood coagulation-related proteins such as staphylocoagulase, and von Willebrand factor-binding proteins were identified. These proteins are implicated in the onset of sepsis and toxic shock syndrome, characterized by intravascular blood coagulation, as well as vascular diseases including acute coronary syndrome and stroke, caused by thrombus formation within a coronary artery, deep vein thrombosis and pulmonary embolism. Also found in the extracellular vesicles are *S. aureus* IgG-binding protein (SbI) that can endow the bacteria with the function of immune evasion by inhibiting the phagocytosis of host immune cells that is implicated in the onset of atopic dermatitis by inducing the expression of IL-18 in epidermal cells and increasing serum IgE levels.

TABLE 1

Proteome of *Staphylococcus aureus*-Derived Extracellular Vesicles

| Gi No. | Protein | Function | Specific Function | in-gel method screening | in-solution method screening |
|---|---|---|---|---|---|
| Extracellular secretion protein | | | | | |
| 150375723 | Beta-lactamase | Response to stimulus | Beta-lactamase activity | ✓ | ✓ |
| 21282496 | Extracellular ECM and plasma binding protein | Multi-organism process | Adhesin | | ✓ |
| 21282773 | Alpha-hemolysin | | Cytolysis of cells of another organism | | ✓ |
| 81704164 | Gamma-hemolysin component C | | Hemolysis by symbiont of host erythrocyte | | ✓ |
| 57650962 | IgG-binding protein SbI | | Pathogenesis | ✓ | ✓ |
| 81704132 | Staphylococcal secretory antigen ssaA1 | | Pathogenesis | ✓ | ✓ |
| 81762108 | Staphylococcal secretory antigen ssaA2 | | Pathogenesis | | ✓ |
| 21281935 | Staphylocoagulase precursor | | Coagulation | ✓ | ✓ |
| 57652487 | Staphylocoagulase precursor | | Coagulation | ✓ | ✓ |
| 37088995 | Staphopain A | | Proteolysis | | ✓ |
| 21284294 | N-acetylmuramoyl-L-alanine amidase | Cellular processes | Cell wall organization | ✓ | ✓ |
| 21282322 | Hypothetical protein MW0593 | | Cell wall organization | | ✓ |
| 81762626 | Bifunctional autolysin | | Cell wall organization | ✓ | ✓ |

TABLE 1-continued

Proteome of *Staphylococcus aureus*-Derived Extracellular Vesicles

| Gi No. | Protein | Function | Specific Function | in-gel method screening | in-solution method screening |
|---|---|---|---|---|---|
| 21284065 | Hypothetical protein MW2336 | Localization | Transport | | ✓ |
| 21283931 | Hydroxamate siderophore binding lipoprotein | | High-affinity iron ion transport | ✓ | ✓ |
| 38604669 | Lipase 2 | Metabolism | Lipid catabolic process | | ✓ |
| 57651231 | 5'-nucleotidase | Poorly characterized | N.A.[e)] | ✓ | ✓ |
| 21282013 | Hypothetical protein MW0284 | | N.A. | ✓ | ✓ |
| 57651320 | Hypothetical protein SACOL0479 | | N.A. | | ✓ |
| 21282306 | Hypothetical protein MW0577 | | N.A. | | ✓ |
| 21283609 | Truncated cell surface protein map-w | | N.A. | ✓ | ✓ | membrane protein

| 21282793 | Penicillin-binding protein 1 | Response to stimulus Cellular processes | Response to antibiotics Peptidoglycan-based cell wall biogenesis | | ✓ |
| 21283069 | PBP2 | Response to stimulus Cellular processes | Response to antibiotics Peptidoglycan-based cell wall biogenesis | | ✓ |
| 21283233 | Penicillin-binding protein 3 | Response to stimulus Cellular processes | Response to antibiotics Peptidoglycan-based cell wall biogenesis | | ✓ |
| 21282494 | Truncated secreted von Willebrand factor-binding protein VWbp | Multi-organism process | Coagulation | | ✓ |
| 21282495 | Truncated secreted von Willebrand factor-binding protein VWbp | | Coagulation | | ✓ |
| 21283671 | Hypothetical protein MW1942 | | Cytolysis of cells of another organism | ✓ | ✓ |
| 21283666 | Staphylococcal enterotoxin SeQ | | Pathogenesis | | ✓ |
| 61213890 | 77 kDa membrane protein | | Pathogenesis | ✓ | |
| 81704700 | N-acetylmuramoyl-L-alanine amidase sle1; Precursor | Cellular processes | Cell wall biogenesis/degradation | ✓ | ✓ |
| 81704612 | Glycerol phosphate lipoteiehoic acid synthase | | Cell wall biogenesis/degradation | ✓ | ✓ |
| 21283316 | Bifunctional preprotein translocase subunit SecD/SecF | Localization | Protein transport | ✓ | ✓ |
| 60392183 | Membrane-bound ribosome protein complex 50 kDa subunit | Metabolism | Glycolysis | ✓ | ✓ |
| 21284194 | Hypothetical protein MW2465 | Poorly characterized | N.A. | | ✓ |
| 21284271 | Hypothetical protein MW2542 | | N.A. | ✓ | |
| 73621231 | Regulatory protein msrR | | N.A. | | ✓ |

Cytosolic protein

| 21283575 | ATP-dependent DNA helicase | Response to stimulus | DNA repair | | ✓ |
| 81762575 | Ribosomal RNA large subunit methyltransferase N | Cellular processes | Response to antibiotics rRNA processing | ✓ | |
| 50402228 | Enoylpyruvate transferase 1 | | Peptidoglycan-based cell wall biogenesis | | ✓ |
| 38604895 | DNA gyrase subunit A | Response to stimulus Metabolism | Response to antibiotics DNA metabolic process | | ✓ |
| 54036785 | ATP synthase subunit beta | | ATP biosynthetic process | | ✓ |
| 59799526 | Glutamine synthetase | | Glutamine biosynthetic process | | ✓ |

TABLE 1-continued

Proteome of *Staphylococcus aureus*-Derived Extracellular Vesicles

| Gi No. | Protein | Function | Specific Function | in-gel method screening | in-solution method screening |
|---|---|---|---|---|---|
| 54037697 | Ribose-phosphate pyrophosphokinase | | Nucleotide biosynthetic process | | ✓ |
| 21283340 | Glutamate-1-semialdehyde aminotransferase | | Porphyrin biosynthetic process | | ✓ |
| 60392318 | Glyceraldehyde-3-phosphate dehydrogenase 1 | | Glycolysis | ✓ | ✓ |
| 21282096 | Bifunctional GMP synthase/glutamine amidotransferase protein | | GMP biosynthetic process | | ✓ |
| 21282838 | Hypothetical protein MW1109 | | Glycerol metabolic process | | ✓ |
| 21283766 | Serine hydroxymethyltransferase | | Glycine metabolic process | ✓ | ✓ |
| 21283370 | Pyruvate kinase | | Glycolysis | | ✓ |
| 21283383 | Acetate kinase | | Phosphorylation | ✓ | ✓ |
| 21283307 | Hypothetical protein MW1578 | | Metabolic process | | ✓ |
| 81832404 | NAD-specific glutamate dehydrogenase | | Amino acid metabolic process | | ✓ |
| 54038961 | CTP synthase | | Glutamine metabolic process | | ✓ |
| 38604707 | Pyruvate dehydrogenase E1 component subunit alpha | | Glycolysis | ✓ | ✓ |
| 38604917 | Dihydrolipoyllysine-residue acetyltransferase component of pyruvate dehydrogenase complex | | Glycolysis | ✓ | ✓ |
| 60392857 | Pyruvate dehydrogenase E1 component subunit beta | | Glycolysis | ✓ | ✓ |
| 119390865 | Pyrimidine-nucleoside phosphorylase | | Pyrimidine base metabolic process | ✓ | |
| 21282878 | Transcription elongation factor NusA | Information storage and processing | Regulation of transcription termination | | ✓ |
| 21282422 | Ribonucleotide-diphosphate reductase subunit alpha | | DNA replication | | ✓ |
| 21283872 | DNA-directed RNA polymerase subunit alpha | | Transcription | ✓ | |
| 21282226 | DNA-directed RNA polymerase subunit beta | | Transcription | ✓ | ✓ |
| 21282227 | DNA-directed RNA polymerase subunit beta' | | Transcription | ✓ | ✓ |
| 21282201 | Lysyl-tRNA synthetase | | Lysyl-tRNA aminoacylation | ✓ | |
| 38258392 | Threonyl-tRNA synthetase | | Threonyl-tRNA aminoacylation | | ✓ |
| 21282875 | Prolyl-tRNA synthetase | | Prolyl-tRNA aminoacylation | | ✓ |
| 21283246 | Glycyl-tRNA synthetase | | Glycyl-tRNA aminoacylation | | ✓ |
| 21283570 | Glutamyl-tRNAGln amidotransferase subunit A | | Translation | | ✓ |
| 21282868 | 30S ribosomal protein S2 | | Translation | | ✓ |
| 54039504 | 30S ribosomal protein S3 | | Translation | ✓ | ✓ |
| 21283391 | 30S ribosomal protein S4 | | Translation | ✓ | ✓ |
| 54039545 | 30S ribosomal protein S7 | | Translation | | ✓ |
| 54039108 | 50S ribosomal protein L1 | | Translation | ✓ | ✓ |
| 21283895 | 50S ribosomal protein L2 | | Translation | ✓ | ✓ |
| 21283897 | 50S ribosomal protein L4 | | Translation | | ✓ |
| 50401243 | 50S ribosomal protein L5 | | Translation | | ✓ |
| 21283883 | 50S ribosomal protein L6 | | Translation | | ✓ |
| 21283866 | 50S ribosomal protein L13 | | Translation | | ✓ |
| 21283879 | 50S ribosomal protein L15 | | Translation | | ✓ |
| 81704219 | 50S ribosomal protein L16 | | Translation | ✓ | ✓ |
| 21282853 | 50S ribosomal protein L19 | | Translation | | ✓ |
| 21282326 | 50S ribosomal protein L21 | | Translation | | ✓ |
| 23821722 | Translation initiation factor IF-2 | | Translation | | ✓ |
| 21282231 | Elongation factor G | | Translation | ✓ | ✓ |
| 54037028 | Elongation factor Tu | | Translation | ✓ | ✓ |

TABLE 1-continued

Proteome of *Staphylococcus aureus*-Derived Extracellular Vesicles

| Gi No. | Protein | Function | Specific Function | in-gel method screening | in-solution method screening |
|---|---|---|---|---|---|
| 21282409 | Hypothetical protein MW0680 | Poorly characterized | N.A. | | ✓ |
| 81704520 | Ribonuclease J 1 | | N.A. | ✓ | ✓ |
| 150392829 | Hypothetical protein | | N.A. | ✓ | ✓ |
| | | Protein of which location in cell is not determined | | | |
| 24638020 | Probable malate:quinone oxidoreductase 2 | Metabolism | Tricarboxylic acid cycle | | ✓ |
| 81847838 | NADH dehydrogenase-like protein | | Oxidation reduction | ✓ | ✓ |
| 81704263 | Probable DEAD-box ATP-dependent RNA helicase | Poorly characterized | N.A. | ✓ | ✓ |
| 61213890 | 77 kDa membrane protein | | Pathogenesis | ✓ | |
| 81704700 | N-acetylmuramoyl-L-alanine amidase sle1: Precursor | Cellular processes | Cell wall biogenesis/degradation | ✓ | ✓ |
| 81704612 | Glycerol phosphate lipoteichoic acid synthase | | Cell wall biogenesis/degradation | ✓ | ✓ |
| 21283316 | Bifunctional preprotein translocase subunit SecD/SecF | Localization | Protein transport | ✓ | ✓ |
| 60392183 | Membrane-bound ribosome protein complex 50 kDa subunit | Metabolism | Glycolysis | ✓ | ✓ |
| 21284194 | Hypothetical protein MW2465 | Poorly characterized | N.A. | | ✓ |
| 21284271 | Hypothetical protein MW2542 | | N.A. | ✓ | |
| 73621231 | Regulatory protein msrR | | N.A. | | ✓ |
| | | 세포질 내 단백질 | | | |
| 21283575 | ATP-dependent DNA helicase | Response to stimulus | DNA repair | | ✓ |
| 81762575 | Ribosomal RNA large subunit methyltransferase N | Cellular processes | Response to antibiotics rRNA processing | ✓ | |
| 50402228 | Enoylpyruvate transferase 1 | | Peptidoglycan-based cell wall biogenesis | | ✓ |
| 38604895 | DNA gyrase subunit A | Response to stimulus Metabolism | Response to antibiotics DNA metabolic process | | ✓ |
| 54036785 | ATP synthase subunit beta | | ATP biosynthetic process | | ✓ |
| 59799526 | Glutamine synthetase | | Glutamine biosynthetic processs | | ✓ |
| 54037697 | Ribose-phosphate pyrophosphokinase | | Nucleotide biosynthetic process | | ✓ |
| 21283340 | Glutamate-1-semialdehyde aminotransferase | | Porphyrin biosynthetic process | | ✓ |
| 60392318 | Glyceraldehyde-3-phosphate dehydrogenase 1 | | Glycolysis | ✓ | ✓ |
| 21282096 | Bifunctional GMP synthase/glutamine amidotrnsferase protein | | GMP biosynthetic process | | ✓ |
| 21282838 | Hypothetical protein MW1109 | | Glycerol metabloic process | | ✓ |
| 21283766 | Serine hydroxymethyltransferase | | Glycine metabolic process | ✓ | ✓ |
| 21283370 | Pyruvate kinase | | Glycolysis | | ✓ |
| 21283383 | Acetate kinase | | Phosphorylation | ✓ | ✓ |
| 21283307 | Hypothetical protein MW1578 | | Metabolic process | | ✓ |
| 81832404 | NAD-specific gluatamate dehydrogenase | | Amino acid metabolic process | | ✓ |
| 54038961 | CTP synthase | | Glutamine metabolic process | | ✓ |
| 38604707 | Pyruvate dehydrogenase E1 component subunit alpha | | Glycolysis | ✓ | ✓ |

TABLE 1-continued

Proteome of *Staphylococcus aureus*-Derived Extracellular Vesicles

| Gi No. | Protein | Function | Specific Function | in-gel method screening | in-solution method screening |
|---|---|---|---|---|---|
| 38604917 | Dihydrolipoyllysine-residue acetyltransferase component of pyruvate dehydrogenase complex | | Glycolysis | ✓ | ✓ |
| 60392857 | Pyruvate dehydrogenase E1 component subunit beta | | Glycolysis | ✓ | ✓ |
| 119390865 | Pyrimidine-nucleoside phosphorylase | | Pyrimidine base metabolic process | ✓ | |
| 21282878 | Transcription elongation factor NusA | Information storage and processing | Regulation of transcription termination | | ✓ |
| 21282422 | Ribonucleotide-diphosphate reductase subunit alpha | | DNA replication | | ✓ |
| 21283872 | DNA-directed RNA polymerase subunit alpha | | Transcription | ✓ | |
| 21282226 | DNA-directed RNA polymerase subunit beta | | Transcription | ✓ | ✓ |
| 21282227 | DNA-directed RNA polymerase subunit beta' | | Transcription | ✓ | ✓ |
| 21282201 | Lysyl-tRNA synthetase | | Lysyl-tRNA aminoacylation | ✓ | |
| 38258392 | Threonyl-tRNA synthetase | | Threonyl-tRNA aminoacylation | | ✓ |
| 21282875 | Prolyl-tRNA synthetase | | Prolyl-tRNA aminoacylation | | ✓ |
| 21283246 | Glycyl-tRNA synthetase | | Glycyl-tRNA aminoacylation | | ✓ |
| 21283570 | Glutamyl-tRNAGln amidotransferase subunit A | | Translation | | ✓ |
| 21282868 | 30S ribosomal protein S2 | | Translation | | ✓ |
| 54039504 | 30S ribosomal protein S3 | | Translation | ✓ | ✓ |
| 21283391 | 30S ribosomal protein S4 | | Translation | ✓ | ✓ |
| 54039545 | 30S ribosomal protein S7 | | Translation | | ✓ |
| 54039108 | 50S ribosomal protein L1 | | Translation | ✓ | ✓ |
| 21283895 | 50S ribosomal protein L2 | | Translation | ✓ | ✓ |
| 21283897 | 50S ribosomal protein L4 | | Translation | | ✓ |
| 50401243 | 50S ribosomal protein L5 | | Translation | | ✓ |
| 21283883 | 50S ribosomal protein L6 | | Translation | | ✓ |
| 21283866 | 50S ribosomal protein L13 | | Translation | | ✓ |
| 21283879 | 50S ribosomal protein L15 | | Translation | | ✓ |
| 81704219 | 50S ribosomal protein L16 | | Translation | ✓ | ✓ |
| 21282853 | 50S ribosomal protein L19 | | Translation | | ✓ |
| 21282326 | 50S ribosomal protein L21 | | Translation | | ✓ |
| 23821722 | Translation initiation factor IF-2 | | Translation | | ✓ |
| 21282231 | Elongation factor G | | Translation | ✓ | ✓ |
| 54037028 | Elongation factor Tu | | Translation | ✓ | ✓ |
| 21282409 | Hypothetical protein MW0680 | Poorly characterized | N.A. | | ✓ |

Example 11

Ex Vivo Innate Immune Response of Macrophages to *Staphylococcus aureus*-Derived Extracellular Vesicles Mouse macrophages (RAW 264.7) were seeded at a density of $1 \times 10^5$ cells/well into 24-well plates and maintained for 24 hours. The cells were washed once with PBS and incubated for hours with 1, 10, 100, 1000 and 10000 ng/ml of *Staphylococcus aureus*-derived extracellular vesicles isolated as in Example 2 in 10% FBS/RPMI in each well. The culture media were collected and centrifuged at 4° C. and 500×g for 10 min. The supernatant was centrifuged again at 3000×g for 20 min. Cytokines present in the resulting supernatant were quantitatively analyzed using ELISA (enzyme linked immunosorbant assay).

Figure 15:
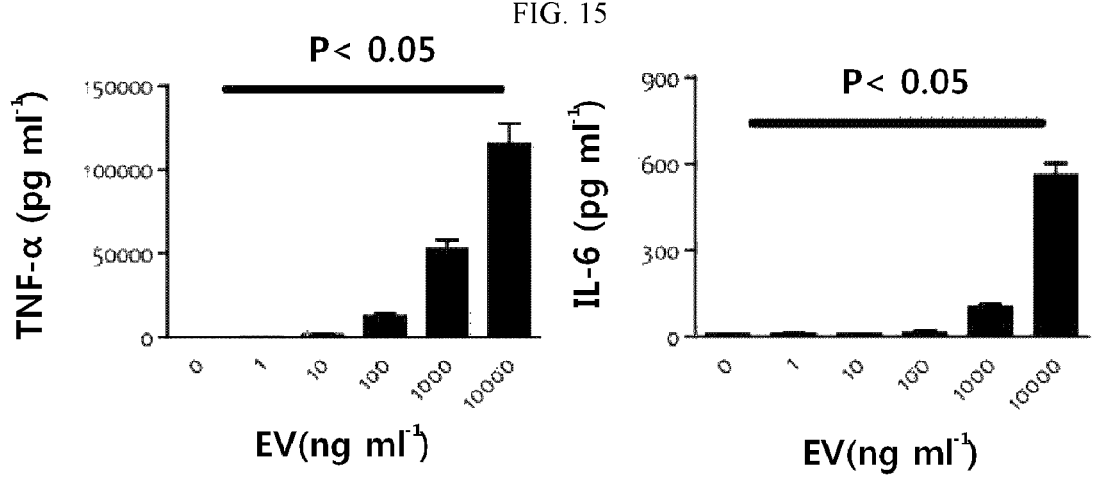
FIG. 15 is of graphs showing that the expression levels of the inflammatory cytokines TNF-α and IL-6 increase with an increase in the concentration of the *Staphylococcus aureus*-derived extracellular vesicles applied to mouse macrophages.

FIG. 15 shows the cytokine levels. As can be seen, the expression levels of the inflammatory cytokines TNF-α and IL-6 increase with an increase in the concentration of the extracellular vesicles, indicating that the *Staphylococcus aureus*-derived extracellular vesicles elicit the innate immune response of macrophages and thus cause inflammation in the host.

Example 12

Ex Vivo Innate Immune Response of Dermal Fibroblasts to *Staphylococcus aureus*-Derived Extracellular Vesicles After removal of the epidermis from mouse dermal tissues, fibroblasts were released from the remaining dermis by enzymatic treatment with trypsin. The fibroblasts were seeded at a density of 1×10⁴ cells per well into 24-well plates and maintained for 24 hours. Afterwards, the cells were incubated for 24 hours with 1 and 10 μg/ml of *Staphylococcus aureus*-derived extracellular vesicles in DMEM. The culture media were collected and centrifuged. ELISA (Enzyme Linked Immunosorbent Assay) was performed on the supernatant to determine the levels of inflammatory cytokines (TNF-α, IL-6) and the cytokines (TSLP) and chemokines (MIP-1α, Eotaxin) that affect adaptive immunity. The results are depicted in FIG. 16.

Figure 16:
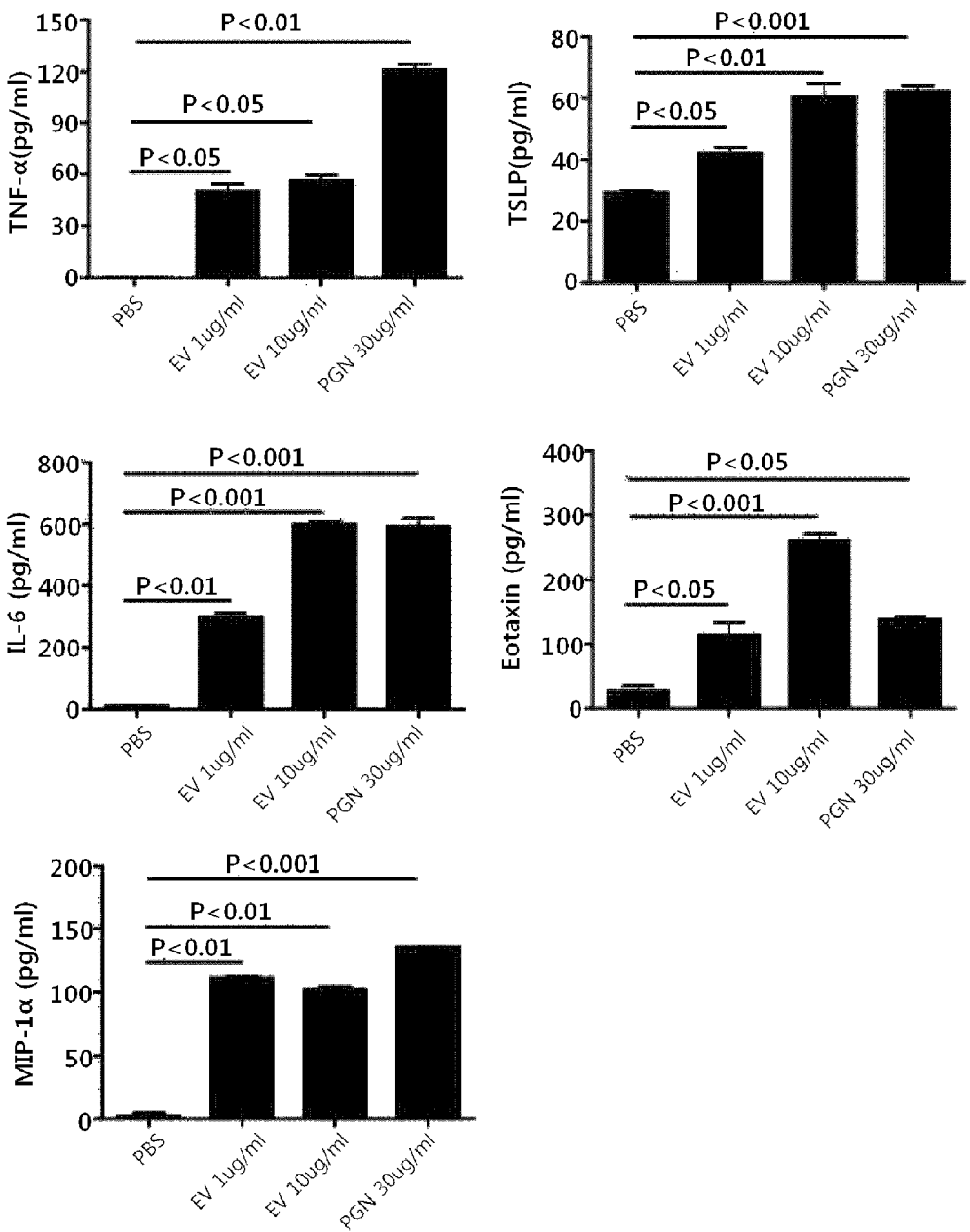
FIG. 16 is of graphs showing the expression levels of various inflammatory mediators in mouse fibroblast cells treated with *Staphylococcus aureus*-derived extracellular vesicles.

FIG. 16 shows that *Staphylococcus aureus*-derived extracellular vesicles stimulate the expression of immune and inflammatory cytokines. As is understood from the data of FIG. 16, *Staphylococcus aureus*-derived extracellular vesicles act on dermal fibroblasts to induce the expression of inflammatory cytokines and the attraction of various immune cells, thereby causing inflammation.

Example 13

Figure 17:
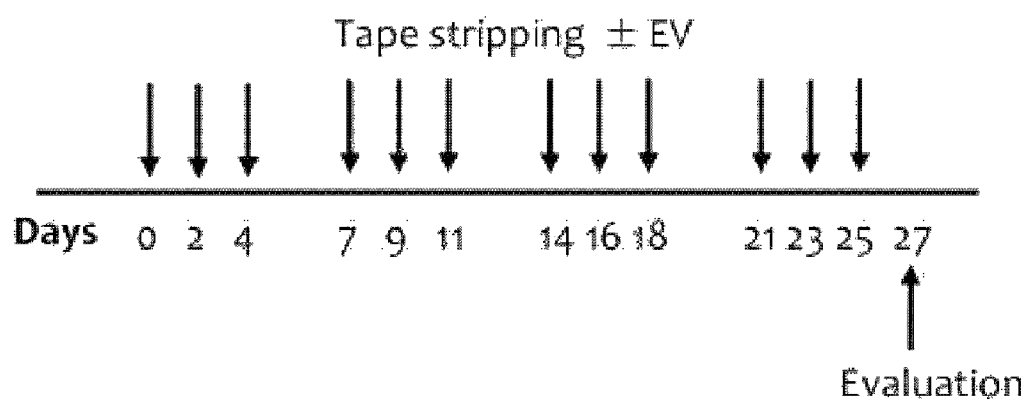
FIG. 17 is a diagram showing an experimental protocol for causing a atopic dermatitis-like symptom in which *Staphylococcus aureus*-derived extracellular vesicles are applied three times a week for 4 weeks to a mouse skin and various indices are evaluated 48 hours after the final application.
Figure 18:
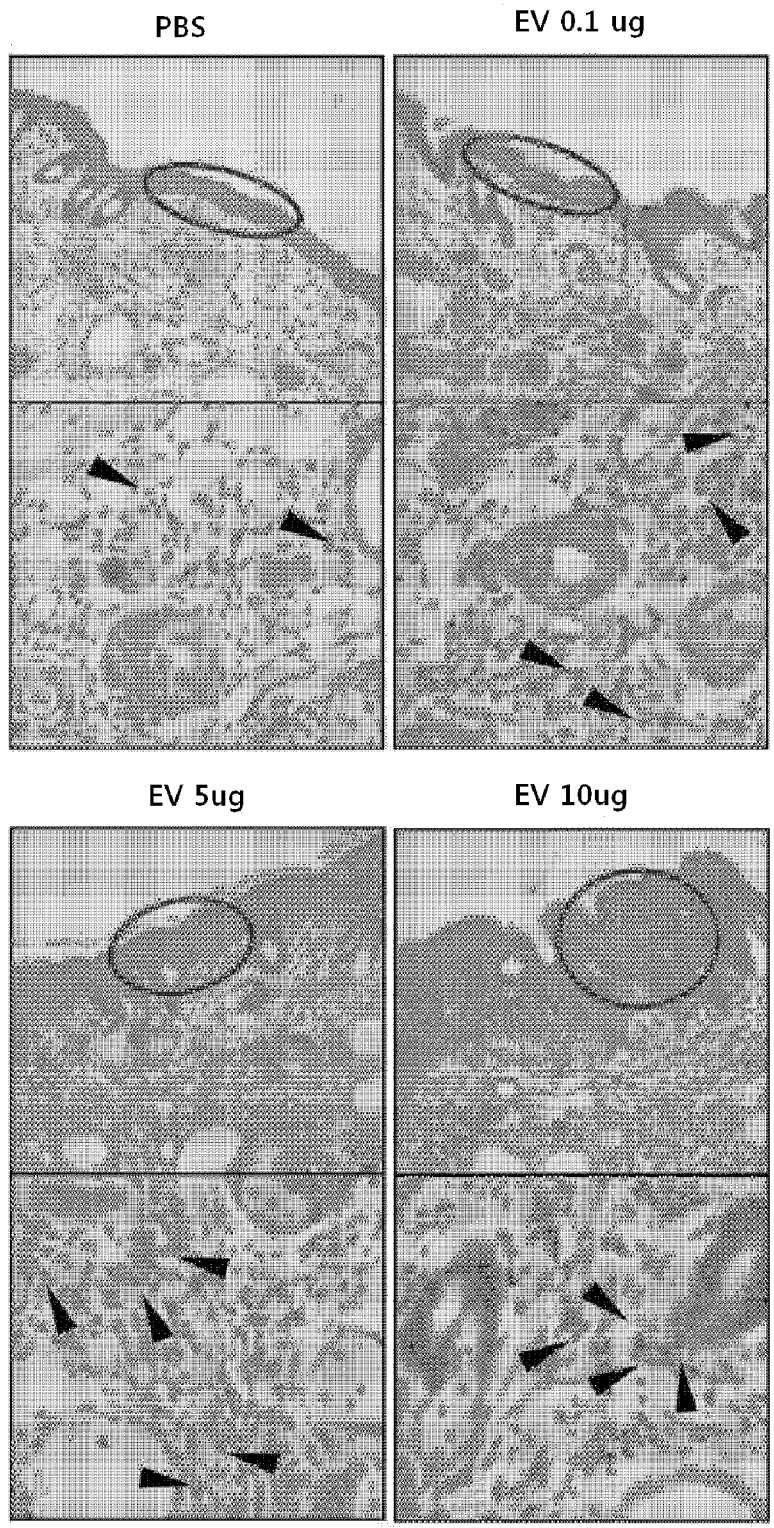
FIG. 18 shows atopic dermatitis-like symptoms including epidermal thickening (red circles) and neutrophilic infiltration (arrow heads) after *Staphylococcus aureus*-derived extracellular vesicles are applied to a mouse skin according to the protocol of FIG. 17.
Figure 19:
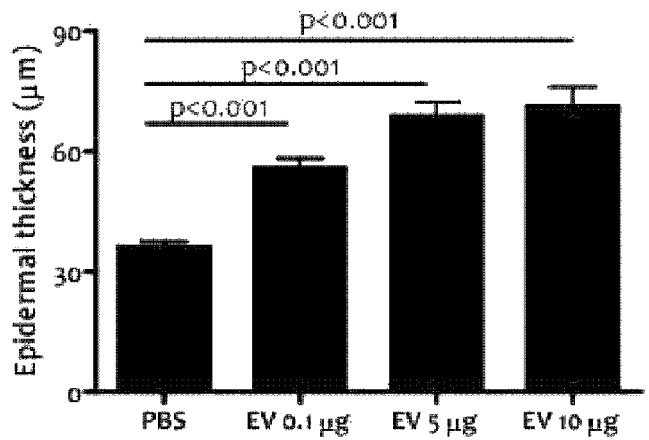
FIG. 19 is of graphs showing numerical evaluations of the symptoms observed in FIG. 18, wherein the epidermal thickness and the counts of infiltrating mast cells and neutrophils are increased by *Staphylococcus aureus*-derived extracellular vesicles.
Figure 19:
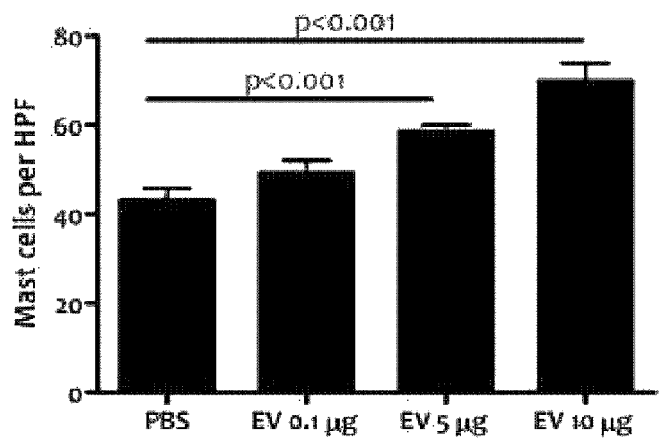
Figure 19:
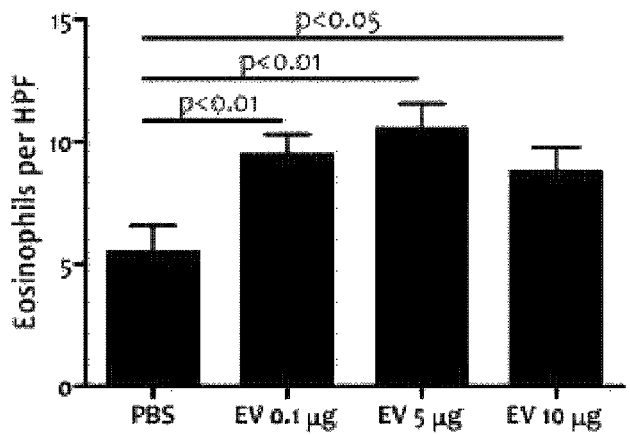
Figure 20:
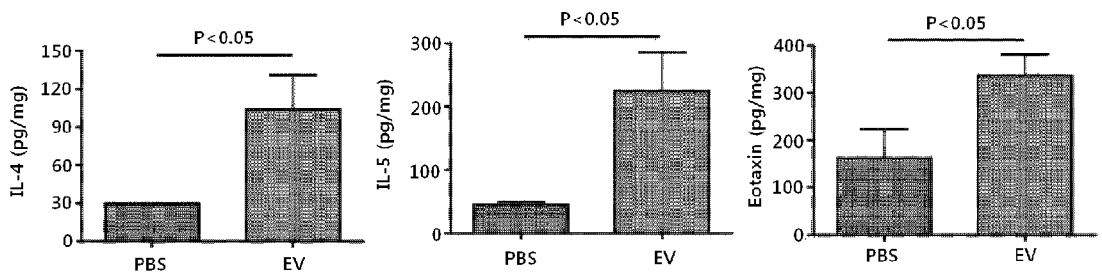
FIG. 20 is of graphs showing the levels of inflammatory cytokines in mouse skin treated with *Staphylococcus aureus*-derived extracellular vesicles in accordance with FIG. 17, where the levels of inflammatory cytokines increase with an increase in the concentration of the vesicles.

Establishment of Animal Model of Atopic Dermatitis with *Staphylococcus aureus*-Derived Extracellular Vesicles The dorsal skin of mice (SKH-HR1, female) was stripped four to six times using Durapore tape (3M). Gauze (2 cm×2 cm) soaked with 0.1 μg, 5 μg and 10 μg of *S. aureus*-derived extracellular vesicles in 100 μl of phosphate buffered saline (PBS) was then placed on the stripped skin and fixed with Tegaderm bio-occlusive tape (3M). This process was repeated three times a week for four weeks. The mice were euthanized 24 hours after the final challenge and the dermal tissues were excised (FIG. 17). Histological analysis showed that the application of *Staphylococcus aureus*-derived extracellular vesicles to the tape-stripped skin induced atopic dermatitis-like inflammation, including epidermal thickening and infiltration of the dermis by inflammatory cells. As with dermal infiltration by inflammatory cells, significantly higher numbers of both eosinophils and mast cells were found in the dermis of mice treated with *Staphylococcus Aureus*-derived extracellular vesicles, compared to saline-treated controls. Together, these data suggest that the application of *Staphylococcus aureus*-derived extracellular vesicles to tape-stripped skin induces atopic disease-like inflammation (FIGS. 18 and 19). In addition, analysis of the type 2 helper T cell (Th2) immune responses, responsible for atopic dermatitis, in dermal tissues showed that in vitro stimulation of fibroblasts with *S. aureus* EV increased the secretion of the Th2-type cytokines, such as IL-4 and IL-5 as well as the chemokine eotoxin, which is induced by the cytokines (FIG. 20).

Example 14

Quantification of *Staphylococcus aureus*-Derived Extracellular Vesicles in Skin Lavage Fluid of Atopic Dermatitis Patients Skin lavage fluids were obtained by rinsing atopic dermatitis patients' skin lesions several times with sterile PBS. To remove bacteria and other debris, 40 ml of the skin lavage fluid was centrifuged at 5000×g and 10 000×g. After centrifugation, the supernatants were filtered through 0.45 μm and 0.22 μm in series. Then, lavage fluids were concentrated to 1 ml using Centriprep with 100 kD cut-off. Some of the concentrate (lavage fluid) was stored while the remainder was mixed with the equal volume of sterile saline and ultracentrifuged at 150,000×g to give extracellular vesicles (EV fraction) as a pellet.

In order to examine whether *Staphylococcus aureus*-derived extracellular vesicles (SA_EV) exist in the skin lavage fluid and the EV fraction, proteins characteristic of *Staphylococcus aureus*-derived extracellular vesicles were analyzed by ELISA using *Staphylococcus aureus*-derived extracellular vesicles-specific antibodies. In this regard, 96-well ELISA plates were coated with anti-*Staphylococcus aureus*-derived extracellular vesicles-specific polyclonal antibodies and blocked with 1% BSA (Bovine Serum Albumin). The concentrated lavage fluids and the EV fraction were added to each well. After incubation for 2 hours, the wells were washed with Tween in PBS. Then, biotinylated anti-*S. aureus* EV-specific polyclonal antibodies were added to each well and incubated for 2 hours. After treatment with streptavidin-conjugated horseradish peroxidase (HRP), chemiluminescence substrates (BM-POD) were added to react with HRP. Luminescence was measured and expressed as RLU.

Figure 21:
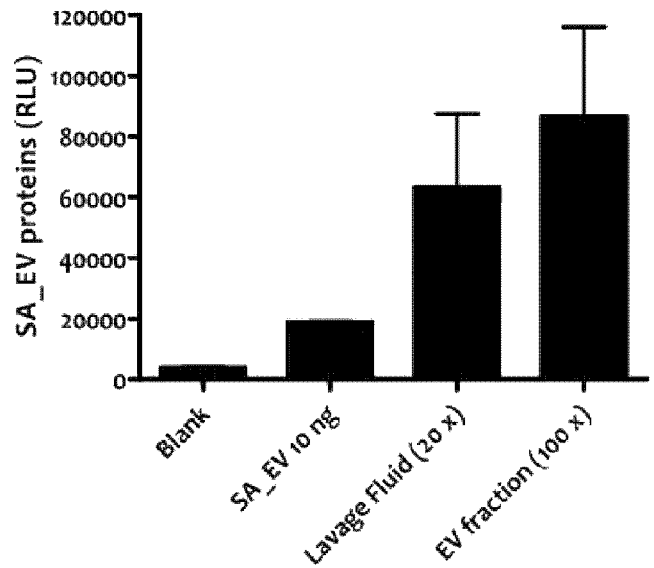
FIG. 21 is graph showing the presence of antigens characteristic of *Staphylococcus aureus*-derived extracellular vesicles in a skin lavage fluid of atopic dermatitis patients, as measured by ELISA.

FIG. 21 is a graph showing the presence of antigens characteristic of *Staphylococcus aureus*-derived extracellular vesicles in the skin lavage fluid of the patient. Also, the data obtained with the EV fraction from the lavage fluid confirmed the presence of *Staphylococcus aureus*-derived extracellular vesicles in the lesions of atopic dermatitis patients.

Example 15

Serum *Staphylococcus aureus*-Derived Extracellular Vesicle-Specific Antibody (IgE) Level of Atopic Dermatitis Patients Blood samples were taken from an atopic dermatitis patient group and an age-matched healthy control group, each consisting of 20 persons 0-10 years old, and centrifuged at 4° C. and 3,500×g for 10 min to give sera.

Figure 22:
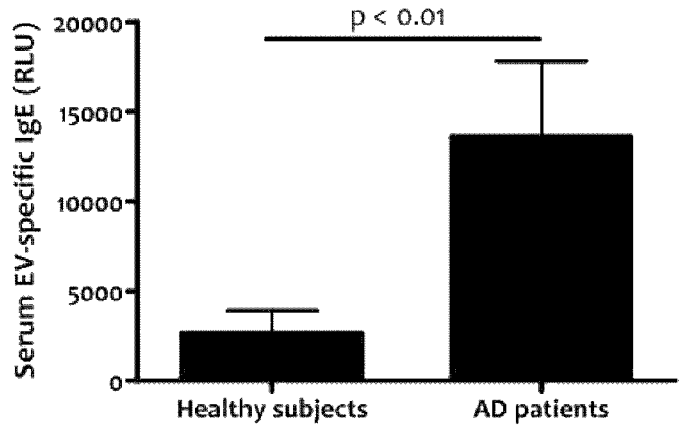
FIG. 22 is a graph showing that the level of *Staphylococcus aureus*-derived extracellular vesicle-specific IgE antibodies was significantly elevated in the sera of the atopic dermatitis patients over that of the healthy control.

FIG. 22 is a graph showing levels of IgG1 and IgE antibodies against the extracellular vesicles in sera as measured by ELISA. As can be seen, the level of *Staphylococcus aureus*-derived extracellular vesicle-specific IgE antibodies was significantly elevated in the sera of the atopic dermatitis patients over that of the healthy control.

Example 16

Figure 23:
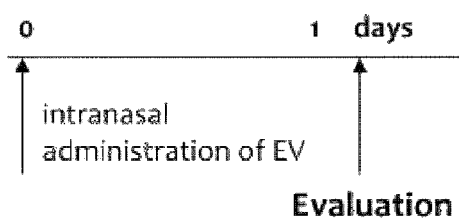
FIG. 23 is a diagram showing a protocol for evaluating the innate immunity induced upon the intranasal administration of *Staphylococcus aureus*-derived extracellular vesicles.
Figure 24:
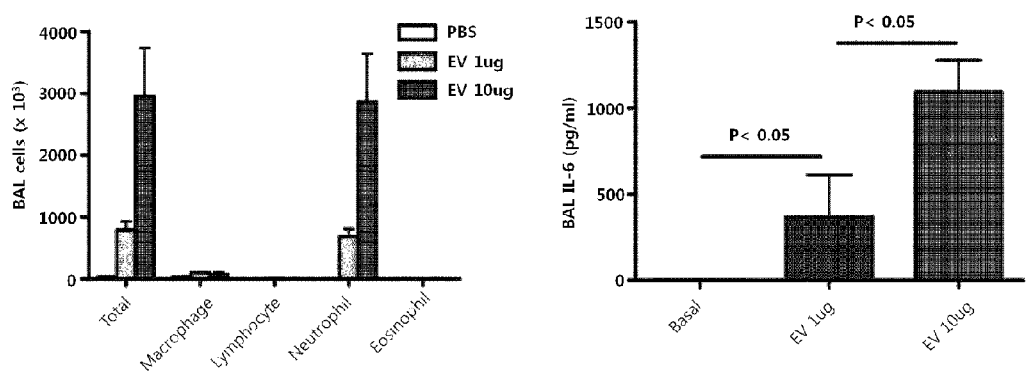
FIG. 24 is of graphs showing that the levels of inflammatory cells and cytokine IL-6 were significantly elevated in the bronchoalveolar lavage fluid of the mice inhaled with *Staphylococcus aureus*-derived extracellular vesicles according to the protocol of FIG. 13 over that of the control.

Induction of Mucosal Th17-Mediated Inflammation by *Staphylococcus aureus*-Derived Extracellular Vesicles Mice were anesthetized with ketamine and rompun and administered with 1 μg and 10 μg of *Staphylococcus aureus*-derived extracellular vesicles in 30 μL of PBS via the nasal route. To examine the effect of *Staphylococcus aureus*-derived extracellular vesicles on innate immunity, BAL fluids were obtained by washing the airway with 1 mL of PBS 24 hours after administration (FIG. 23). Quantitative analyses showed that the levels of inflammatory cells (especially neutrophils) and IL-6, which is an inflammatory cytokine inducing a Th17 immune response, in the bronchalvelolar lavage fluid increased with an increase in the concentration of *Staphylococcus aureus*-derived extracellular vesicles (FIG. 24), indicating that *Staphylococcus aureus*-derived extracellular vesicles induces Th17-mediated inflammation on the airway mucus.

Figure 25:
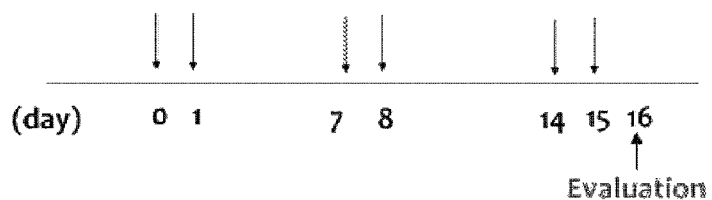
FIG. 25 is a diagram showing a protocol for evaluating the adaptive immunity induced upon the intranasal application of *Staphylococcus aureus*-derived extracellular vesicles.

To examine the adaptive immunity induced by *Staphylococcus aureus*-derived extracellular vesicles, mice were administrated with 1 μg of *Staphylococcus aureus*-derived extracellular vesicles twice a week for three weeks by intranasal inhalation. Bronchoalveolar lavage fluids were obtained 24 hours after the final inhalation, and analyzed for inflammation (FIG. 25).

Figure 26:
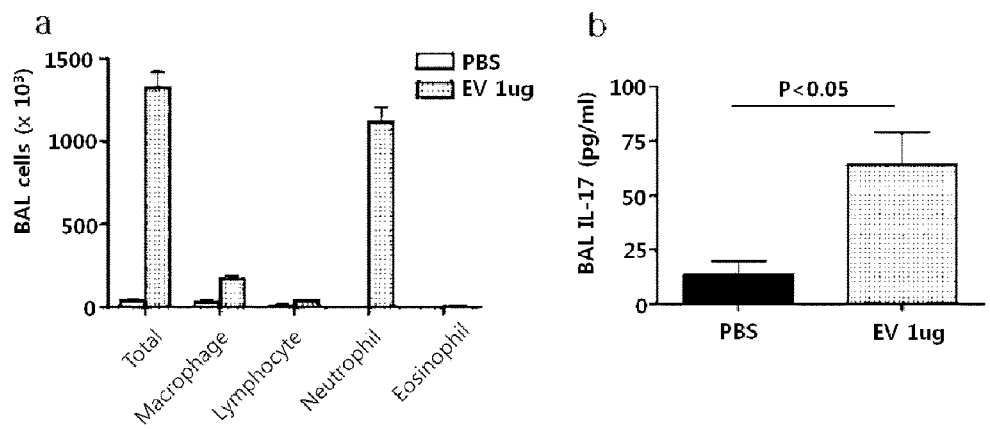
FIG. 26 is of graphs showing the induction of Th17-mediated immunity on the tracheal mucus, wherein that the levels of inflammatory cells and cytokine IL-7 were elevated in the bronchoalveolar lavage fluid of the mice inhaled with *Staphylococcus aureus*-derived extracellular vesicles according to the protocol of FIG. 25 over that of the control.

As is understood from the data of FIG. 26, a greatly increased level of inflammatory cells, especially neutrophils, was found in the bronchoalveolar lavage fluids of the *Staphylococcus aureus*-derived extracellular vesicle-inhaled group, compared to the control group (FIG. 26a). Also, airway mucosal inflammation was determined by measuring cytokine levels in bronchoalveolar lavage fluids, IL-17, which is a cytokine released from Th17 cells, and was seen to significantly increase in the *Staphylococcus aureus*-derived extracellular vesicle-inhaled group (FIG. 26b).

From the data, it can be inferred that when repetitively inhaled, *Staphylococcus aureus*-derived extracellular vesicles act locally to induce neutrophilic inflammation characterized by the Th17 immune response on the airway mucus.

Example 17

Induction of Sepsis by *Staphylococcus aureus*-Derived Extracellular Vesicles

Figure 27:
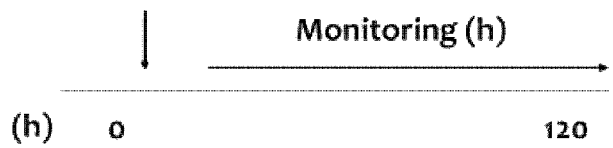
FIG. 27 is a diagram showing an experimental protocol for confirming the lethal dose of *Staphylococcus aureus*-extracellular vesicles in mice.

The extracellular vesicles isolated as in Example 2, were intravenously injected at a dose of 15, 25 or 50 μg into mice (C57B6, male), and dead mice were counted every 12 hours (FIG. 27).

Figure 28:
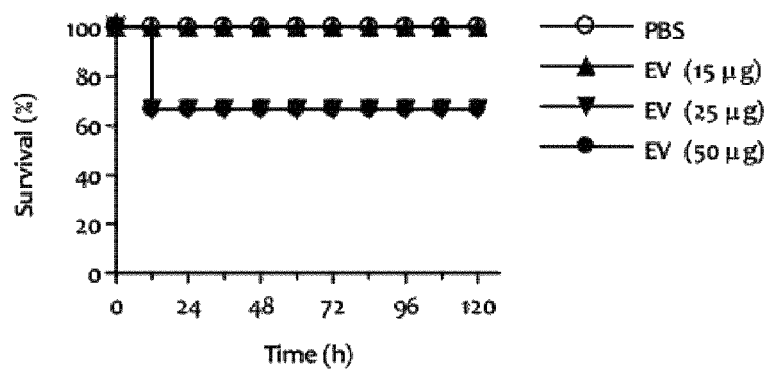
FIG. 28 is a graph showing survival rates of the mice treated with *Staphylococcus aureus*-derived extracellular vesicles.

As can be seen in the survival graph of FIG. 28, the survival rate was reduced to 66.6% in the mice groups administered with 25 μg and 50 μg of the extracellular vesicles. That is, a certain dose of the extracellular vesicles is lethal to mice.

Figure 29:
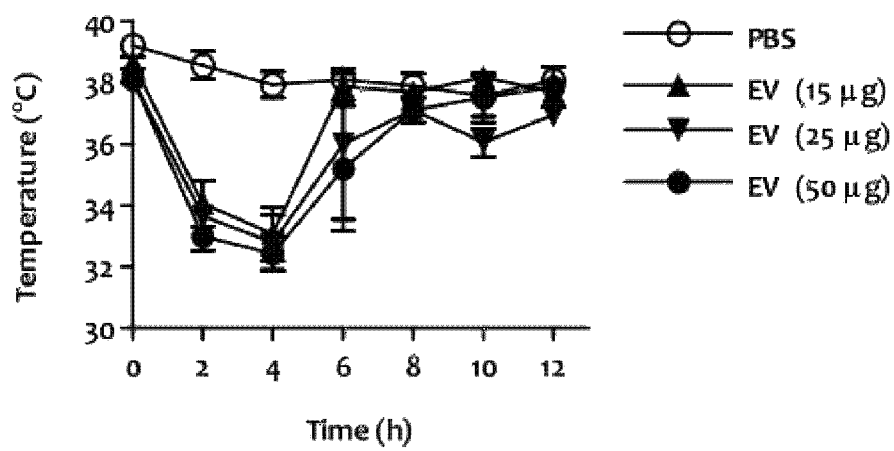
FIG. 29 is a graph showing the induction of hypothermia, an index for systemic inflammation, by *Staphylococcus aureus*-derived extracellular vesicles.

FIG. 29 shows a change in body temperature for 12 hours after the injection of *Staphylococcus aureus*-derived extracellular vesicles (5 μg) into mice (C57B6, male). Body temperatures were recorded every two hours on the digital display of a rectal thermometer applied to the mice. As can be seen, lowered body temperatures (hypothermia), an index for SIRS (systemic inflammatory response syndrome), were detected in the mice administered with 15, 25, and 50 μg of the extracellular vesicles.

Example 18

Figure 30:
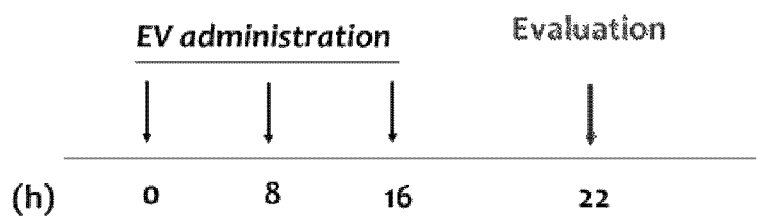
FIG. 30 is a diagram showing a protocol for establishing an animal model of disseminated intravascular coagulation with *Staphylococcus aureus*-derived extracellular vesicles.

Intravascular Coagulation and Thrombosis by *Staphylococcus aureus*-Derived Extracellular Vesicles Mice (C57B6, male) were administered three times at regular intervals of 8 hours with 5 μg of the *Staphylococcus aureus*-derived extracellular vesicles isolated in Example 2 through various routes, and euthanized 6 hours after the final administration, followed by pneumonectomy (FIG. 30). Mice that were injected (IV) with PBS through the tail vein (I.V.) were used as a negative control. The excised lungs were stained with H&E (hematoxylin-Eosin) so that cell nuclei and cytoplasm were stained blue (hematoxylin) and red (eosin), respectively.

Figure 31:
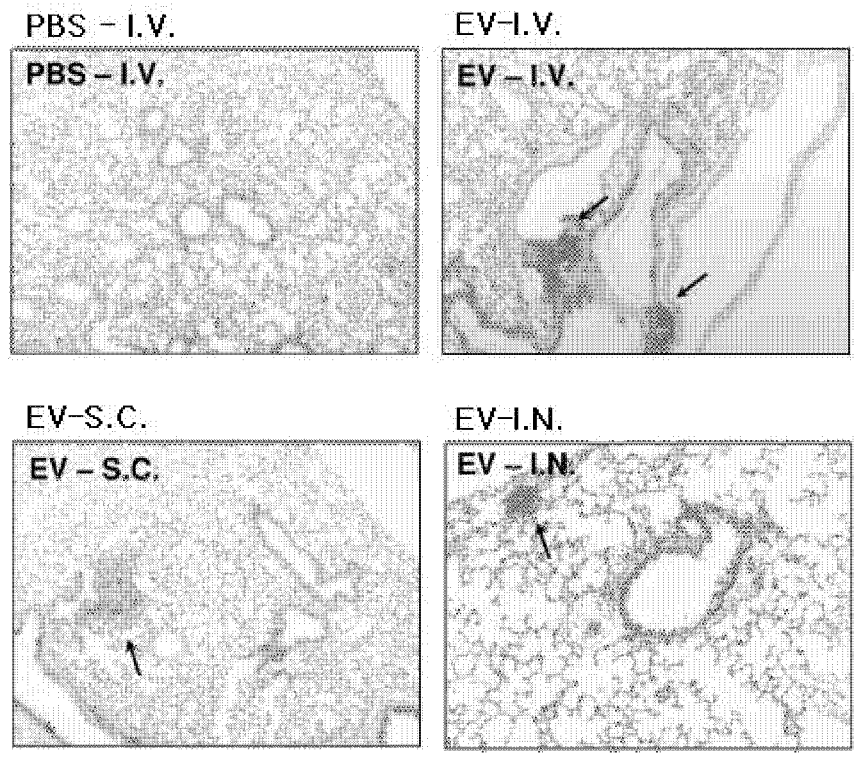
FIG. 31 is of photographs showing H&E-stained pulmonary tissues excised after *Staphylococcus aureus*-derived extracellular vesicles were applied according to the protocol of FIG. 30.

The photographs of FIG. 31 are of H&E-stained tissues, showing the formation of thrombus in the vein after I.V. injection of the extracellular vesicles, the infiltration of inflammatory cells around blood vessels after subcutaneous injection (S.C.), and the formation of thrombus in pulmonary vessels after intranasal administration (I.N.).

Figure 32:
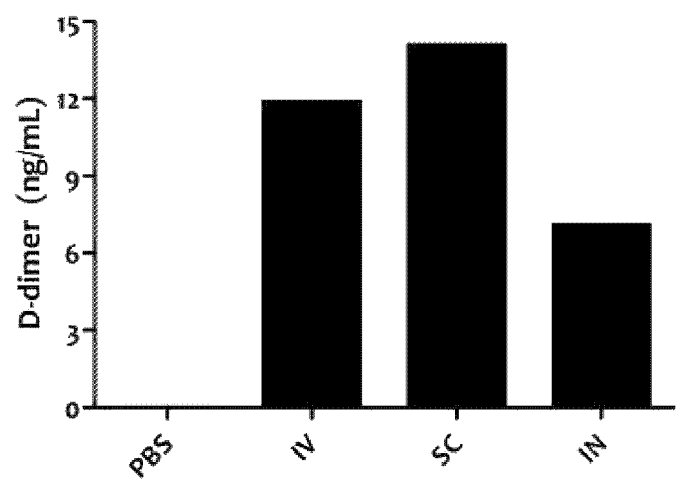
FIG. 32 is a graph showing plasma D-dimer levels measured after *Staphylococcus aureus*-derived extracellular vesicles were applied according to the protocol of FIG. 30.

The index levels of disseminated intravascular coagulation were examined. In this regard, blood samples taken from the mouse heart were mixed at a ratio of 9:1 with the anti-coagulant agent sodium citrate to give plasma. FIG. 32 shows the levels of D-dimer, an index for disseminated intravascular coagulation, as measured by a D-dimer diagnosis kit. The level of D-dimer was observed to increase in all the mice that were administered with the vesicles irrespectively of the route, compared to the control, but was much higher upon I.V. or S.C. injection. Also, platelets, another index for disseminated intravascular coagulation, were counted. In this regard, 1 μl of the blood sample was diluted in 199 μl of 1% ammonium oxalate and allowed to stand for 10 min before counting platelets. The results are depicted in FIG. 33.

Figure 33:
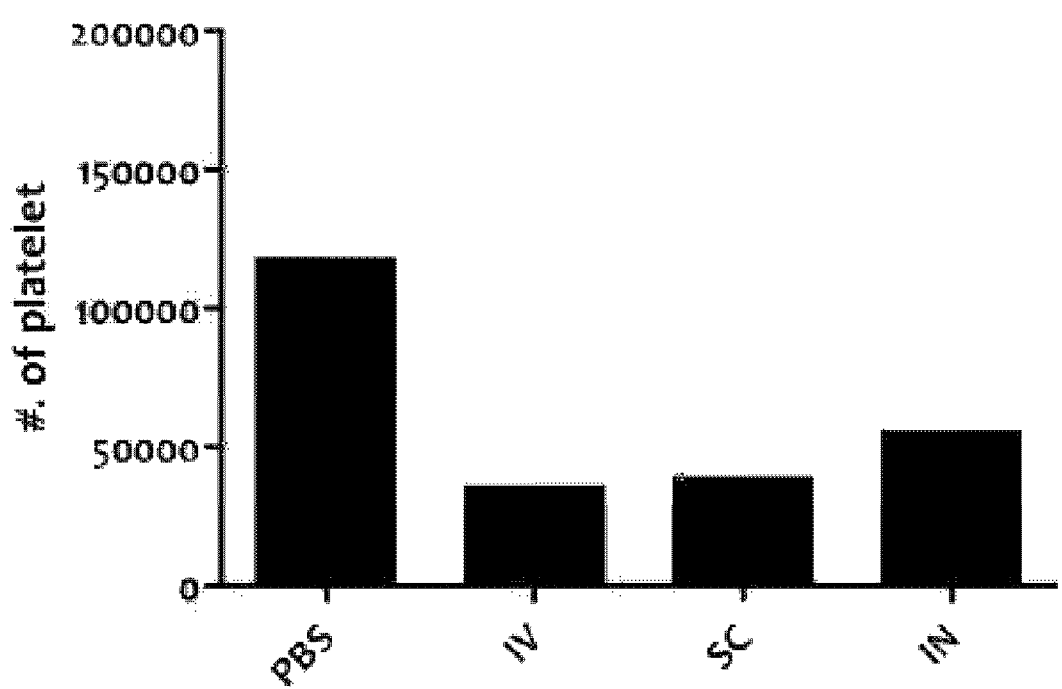
FIG. 33 is a plasma platelet levels measured after *Staphylococcus aureus*-derived extracellular vesicles were applied according to the protocol of FIG. 30.

FIG. 33 shows the occurrence of thrombocytopenia in all extracellular vesicle-administered mice irrespective of administration route.

Example 19

Figure 34:
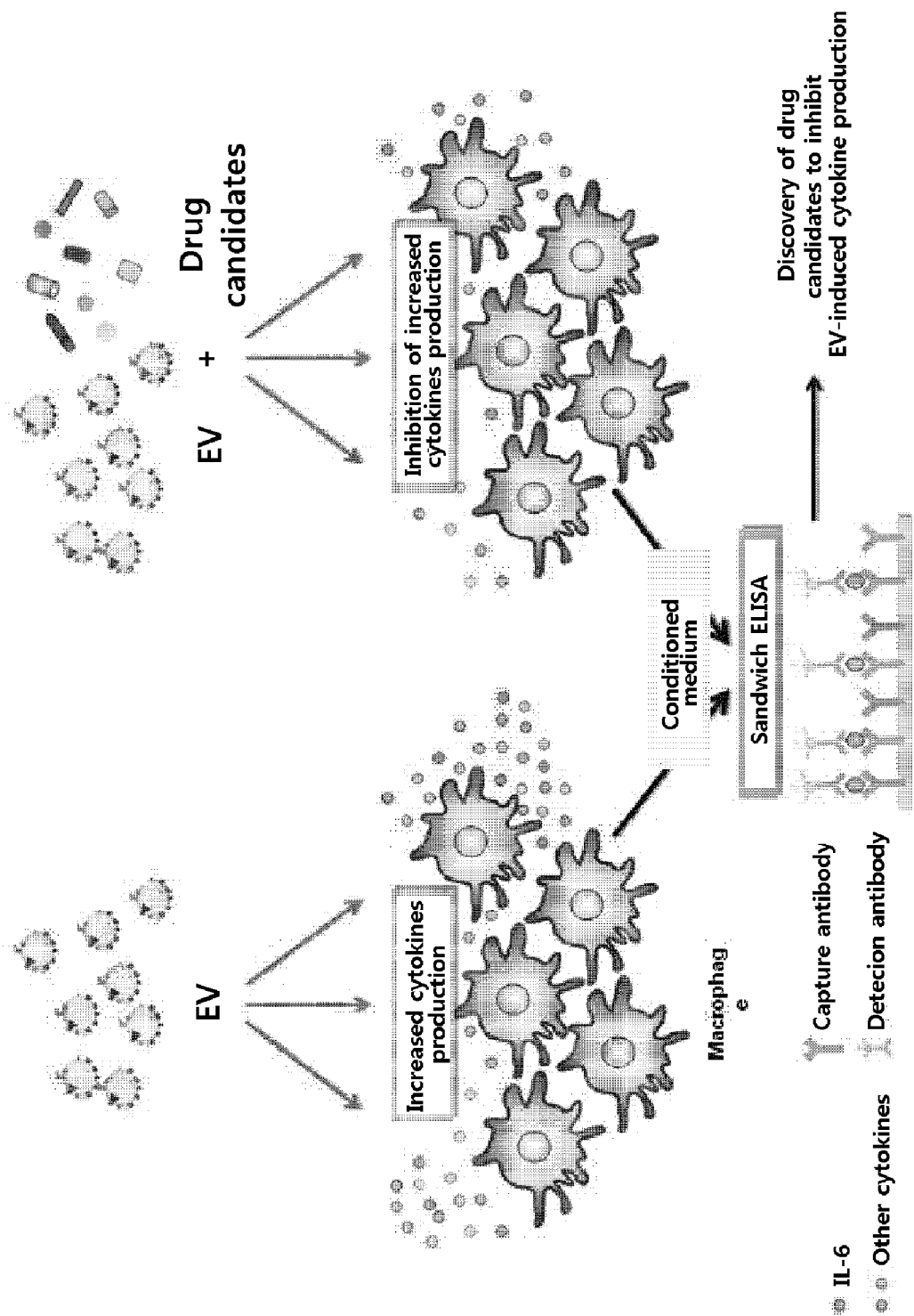
FIG. 34 IS a schematic diagram showing the discovery of drug candidates using *Staphylococcus aureus*-derived extracellular vesicles.

Establishment of In Vitro Screening System for Drug Candidates for Prevention or Treatment of *Staphylococcus aureus*-Derived Extracellular Vesicle-Induced Disease The previous Examples demonstrate that the inflammatory cytokines induced by the mouse *Staphylococcus aureus*-derived extracellular vesicles have a large involvement with the generation of various diseases. Based on this fact, an in vitro screening system was established by which substances inhibitory of inflammatory cytokine activity could be discovered. FIG. 34 is a schematic diagram showing the discovery of substances inhibitory of the *Staphylococcus aureus*-derived extracellular vesicles-induced release of inflammatory cytokines. The mouse macrophages (RAW 264.7) by the method of Example 11, were treated with the *Staphylococcus aureus*-derived extracellular vesicles (1 μg/ml) alone, separated by the method of Example 2, or in combination with a drug candidate (10 μM), for 15 hours in a 37° C. incubator. Then, the culture media was collected and centrifuged at 4° C. and 500×g for 10 min and subsequently at 4° C. and 3000×g for 20 min. IL-6 in the supernatant was quantitatively analyzed by ELISA. These processes account, at least in part, for a method for in vitro screening drug candidates inhibitory of the *Staphylococcus aureus*-derived extracellular vesicle-induced secretion of IL-6, by which drug candidates preventive or therapeutic of *Staphylococcus aureus*-derived extracellular vesicles-caused diseases can be provided.

Example 20

Figure 35:
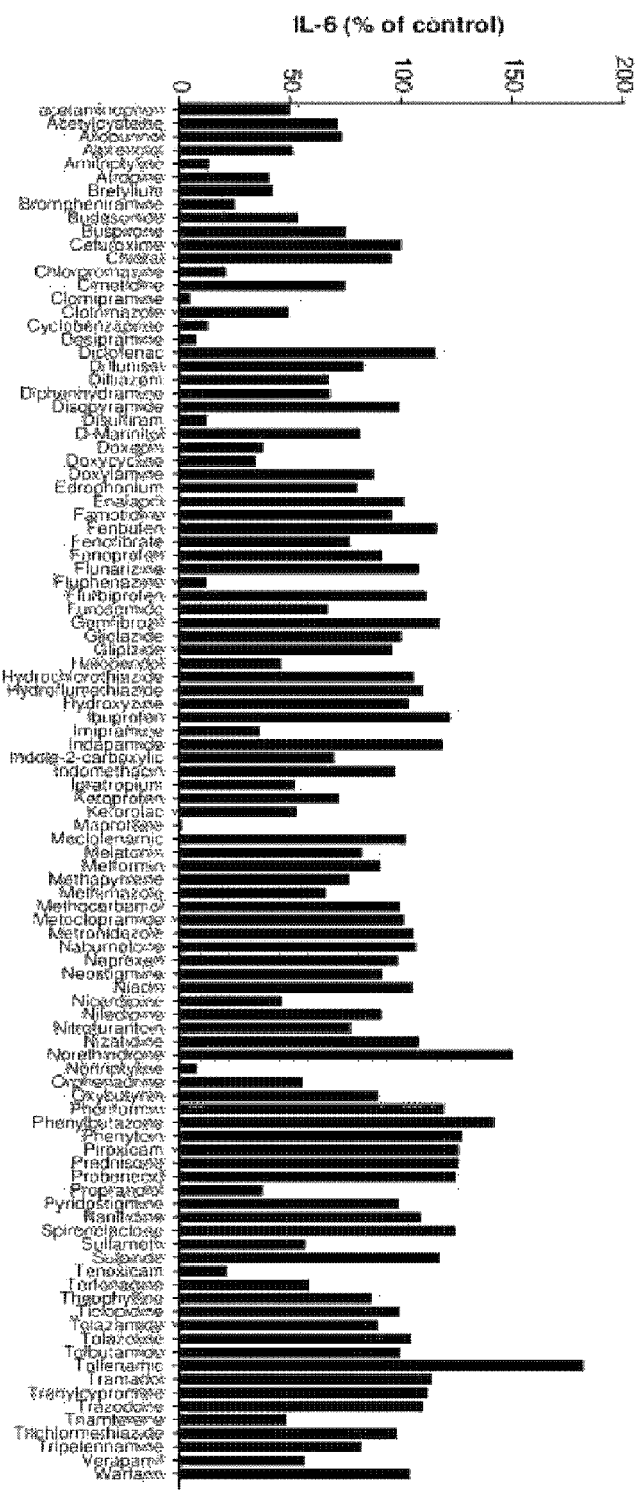
FIG. 35 is a graph showing IL-6 levels of the mouse macrophage cultures as percentages of those of the positive control when the mouse macrophages were treated with *Staphylococcus aureus*-derived extracellular vesicles and prodrugs.

Evaluation of In Vivo Pharmaceutical Efficacy of Prodrugs Discovered by the In Vitro Screening System FIG. 35 shows IL-6 levels of the cell cultures as percentages of those of the positive control when the cell cultures were treated with each of 102 different prodrugs (Acetaminophen, Acetylcysteine, Allopurinol, Alprenolol HCl, Amitriptyline HCl, Atropine, Bretylium tosylate, Brompheniramine, Budesonide, Buspirone HCl, Cefuroxime, Chloral Hydrate, Chlorpromazine HCl, Cimetidine, Clomipramine HCl, Clotrimazole, Cyclobenzaprine, Desipramine HCl, Diclofenac, Diflunisal, Diltiazem, Diphenhydramine HCl, Disopyramide, Disulfuram, D-Mannitol, Doxepin, Doxycycline hydrate, Doxylamine succinate, Edrophonium chloride, Enalapril maleate, Famotidine, Fenbufen, Fenofibrate, Fenoprofen calcium salt hydrate, Flunarizine dihydrochloride, Fluphenazine dichloride, Flurbiprofen, Furosemide, Gemfibrozil, Gliclazide, Glipizide, Haloperidol, Hydrochlorothiazide, Hydroflumethiazide, Hydroxyzine HCl, Ibuprofen, Imipramine HCl, Indapamide, Indole-2-carboxylic acid, Indomethacin, Ipratropium, Ketoprofen, Ketorolac tris salt, Maprotiline HCl, Meclofenamic acid, Melatonin, Metformin, Methapyrilene HCl, Methimazole, Methocarbamol, Metoclopramide HCl, Metronidazole, Nabumetone, Naproxen, Neostigmine Br, Niacin, Nicardipine HCl, Nifedipine, Nitrofurantoin, Nizatidine Norethindrone, Nortriptyline, Orphenadrine HCl, Oxybutynin, Phenformin HCl, Phenylbutazone, Phenyloin, Piroxicam, Prednisone, Probenecid, Propranolol HCl, Pyridostigmine Br, Ranitidine HCl, Spironolactone, Sulfameth, Sulpiride, Tenoxicam, Terfenadine, Theophylline, Ticlopidine HCl, Tolazamide, Tolazoline, Tolbutamide, Tolfenamic acid, Tramadol HCl, Tranylcypromine, Trazodone HCl, Triamterene, Trichlormethiazide, Tripelennamine HCl, Verapamil, Warfarin) as in Example 19. Of them, 19 (Acetaminophen, Amitriptyline HCl, Atropine, Bretylium tosylate, Brompheniramine, Chlorpromazine HCl, Clomipramine HCl, Cyclobenzaprine, Desipramine HCl, Disulfuram, Doxepin, Doxycycline hydrate, Doxylamine succinate, Haloperidol, Imipramine HCl, Nicardipine HCl, Nortriptyline, Propranolol HCl, Tenoxicam) were discovered as drug candidates as they reduced the IL-6 level to below 50% of that of the positive control.

Figure 36:
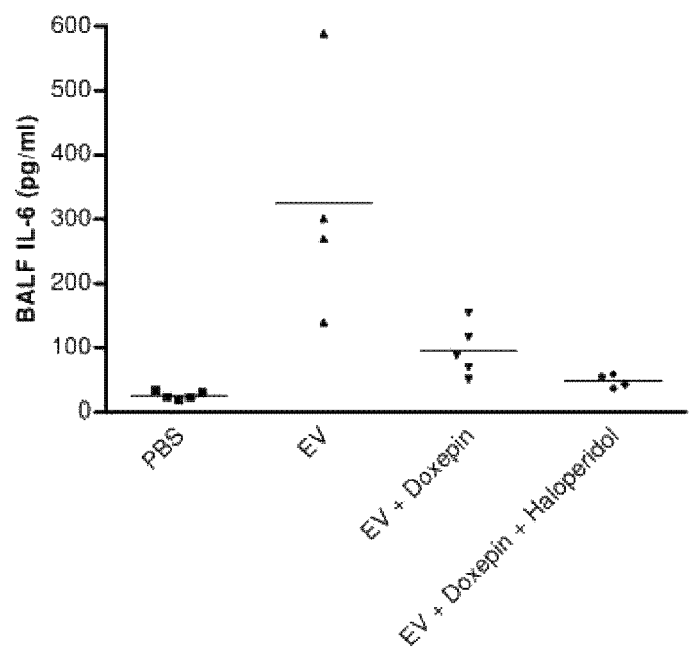
FIG. 36 is a graph showing the levels of IL-6 in the bronchoalveolar lavage fluids obtained after the prodrugs Doxepin and Haloperidol were intraperitoneally injected into mice immunized with the *Staphylococcus aureus*-derived extracellular vesicles by intranasal injection.

FIG. 36 is a graph showing the levels of IL-6, as measured by ELISA, in the bronchoalveolar lavage fluids which were obtained 12 hours after the prodrugs (10 mg/kg) revealed above were intraperitoneally injected into C57BL/6 mouse groups (male, 6 weeks old, 4 mice in each group) immunized with 1 µg of the *Staphylococcus aureus*-derived extracellular vesicles by intranasal injection. Doxepin, discovered by the in vitro screening system, was identified to suppress IL-6 activity and exert a synergistic effect, together with Haloperidol, also discovered by the in vitro screening system.

From these results, it is apparent that the in vitro drug screening system using the *Staphylococcus aureus*-derived extracellular vesicles, established in Example 19, is a very useful method by which drugs can be effectively selected for the prevention or treatment of *Staphylococcus aureus*-derived extracellular vesicle-induced diseases.

Example 21

Figure 37:
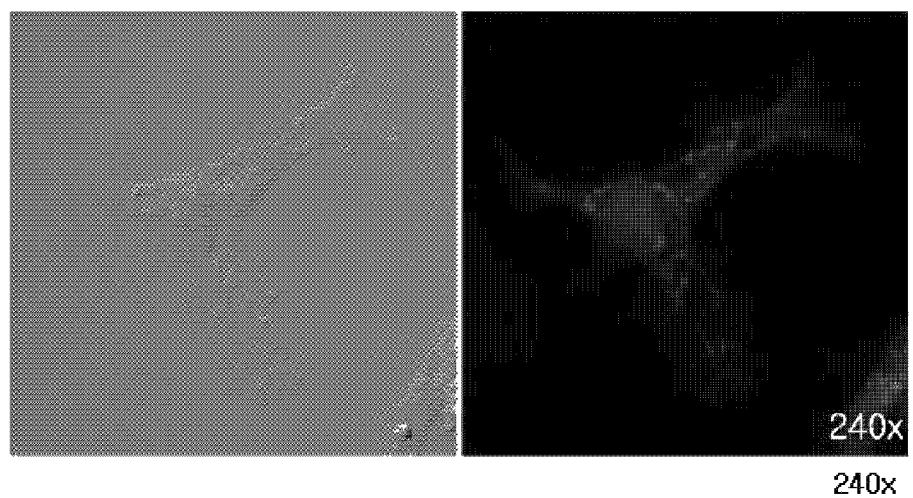
FIG. 37 is of fluorescence microscope images showing the uptake of *Staphylococcus aureus*-derived extracellular vesicles by mouse dendritic cells.

In Vitro Immune Response Induced by *Staphylococcus aureus*-Derived Extracellular Vesicles It was understood from the results of Example 11 that *Staphylococcus aureus*-derived extracellular vesicles elicit immune responses in host cells by stimulating inflammatory cells because mouse macrophages (RAW 264.7) treated with the vesicles secreted IL-6, which stimulates Th17 differentiation. Fluorescence microscopy showed that six hours after they were treated with *Staphylococcus aureus*-derived extracellular vesicles labeled with DiI (1,1'-dioctadecyl-3,3,3'3'-tetramethylindocarbocyanine perchlorate), bone marrow-derived dendritic cells (BMDC) engulfed the vesicles therein (FIG. 37).

Figure 38:
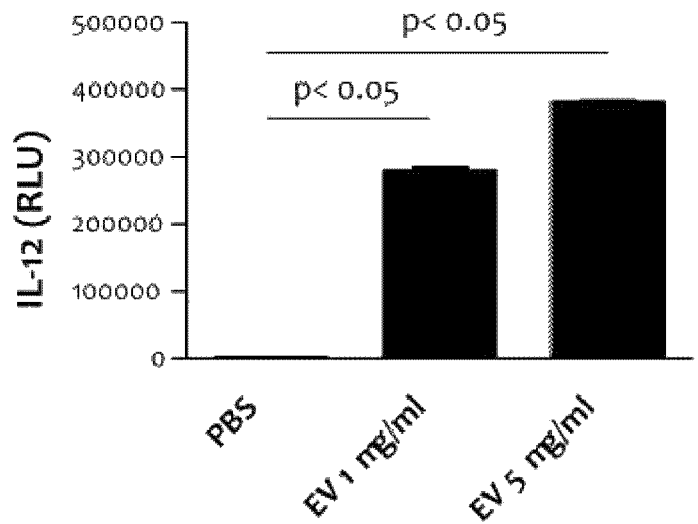
FIG. 38 is a graph showing that *Staphylococcus aureus*-derived extracellular vesicles induced the secretion of the IL-12p40 cytokine from mouse dendritic cells in a dose-dependent manner.
Figure 39:
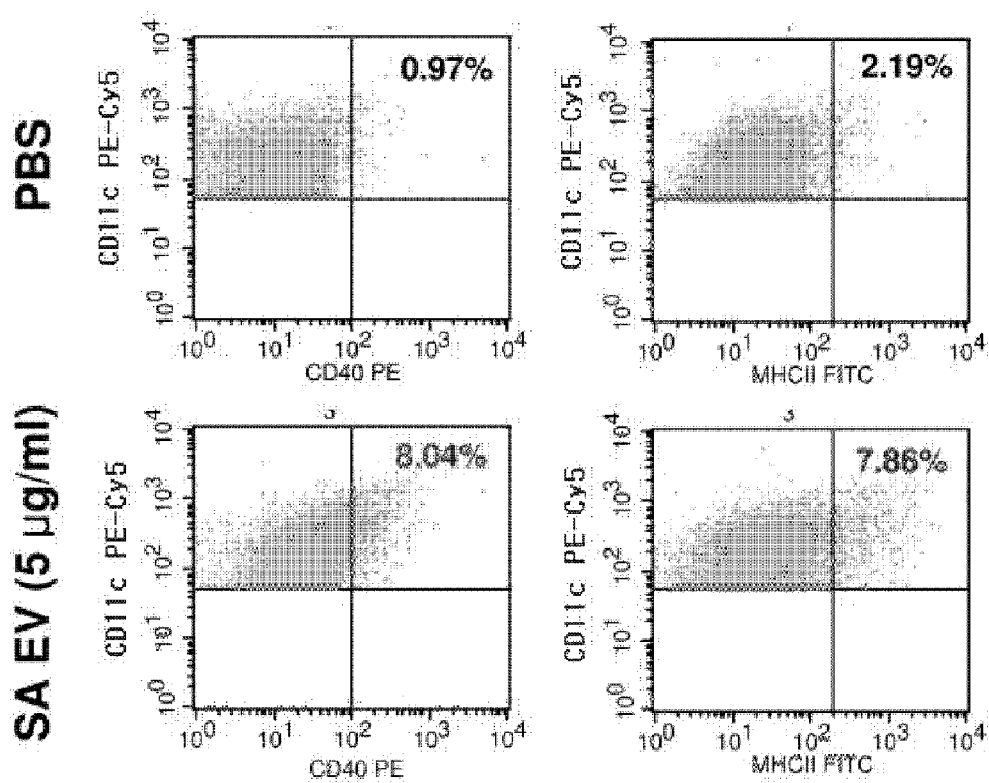
FIG. 39 is of graphs showing that *Staphylococcus aureus*-derived extracellular vesicles induced the expression of CD40 and MHCII on the surface of mouse dendritic cells in a dose-dependent manner.

In addition, after dendritic cells were incubated with the extracellular vesicles for 24 hours, cytokines released to the culture media were quantitatively analyzed by ELISA. As a result, elevated levels were detected for IL-12, a cytokine stimulating Th1 differentiation (FIG. 38) and for CD40 and MHCII, indicative of the activation of dendritic cells (FIG. 39). Together, these results suggest that *Staphylococcus aureus*-derived extracellular vesicles not only act on antibody-presenting cells to enhance adaptive immunity, but also induce T cells to differentiate into Th1 and Th17 cells.

Example 22

Figure 40:
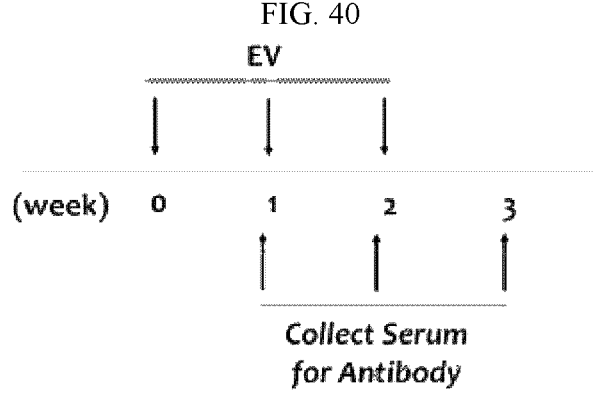
FIG. 40 is a diagram showing a protocol for measuring the level of the antibodies induced by *Staphylococcus aureus*-derived extracellular vesicles.

Induction of Antibody Production and T Cell Immune Response by Subcutaneous Injection of *Staphylococcus aureus*-Derived Extracellular Vesicles To evaluate the *Staphylococcus aureus*-derived extracellular vesicles as a vaccine to induce antibody production, the *Staphylococcus aureus*-derived extracellular vesicles prepared in Example 2 was subcutaneously injected at a dose of 1, 5 or 20 µg into mice (C57B6, male) three times at regular intervals of one week. Blood samples were taken from the ocular blood vessels on weeks 1, 2 and 3 (FIG. 40). The blood samples were coagulated at room temperature for 30 min and centrifuged at 4° C. and 3,500×g for 10 min to take sera as a supernatant.

Figure 41:
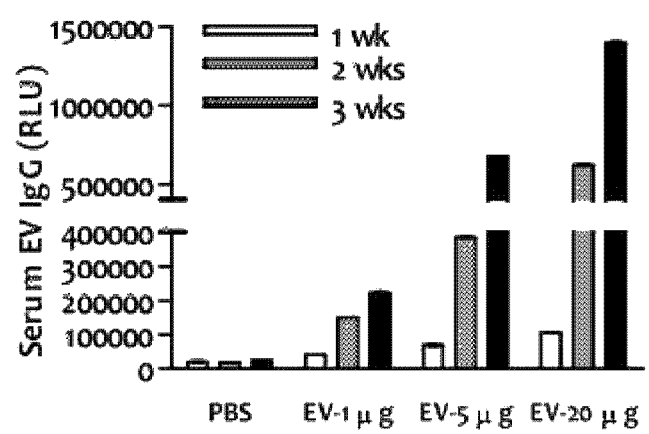
FIG. 41 is a graph showing increased levels of extracellular vesicle-specific IgG antibodies in the mouse sera obtained according to the protocol of FIG. 40.

FIG. 41 is a graph in which ELISA levels of IgG antibody, an index for immune response to the extracellular vesicles, are plotted versus doses of vaccine, showing that antibodies specific for vesicular proteins were produced in a dose-dependent manner, with the antibody titer amplified since the second injection. Thus, two or more subcutaneous injections of the extracellular vesicles induce the production of antibodies specific for proteins of the extracellular vesicles derived from *Staphylococcus aureus*.

Figure 42:
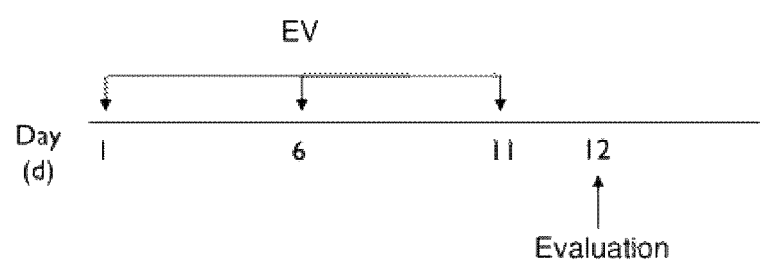
FIG. 42 is a diagram showing a protocol for measuring immunological indices induced in the mice immunized with *Staphylococcus aureus*-derived extracellular vesicles as a vaccine.

To evaluate *Staphylococcus aureus-extracellular* vesicle-induced T cell immune responses, *Staphylococcus aureus*-extracellular vesicles were subcutaneously injected at a dose of 2, 5 or 10 µg into mice (C57B6, male) three times at regular intervals of five days. Immune responses in splenocytes were examined 24 hours after the final injection (FIG. 42).

Figure 43:
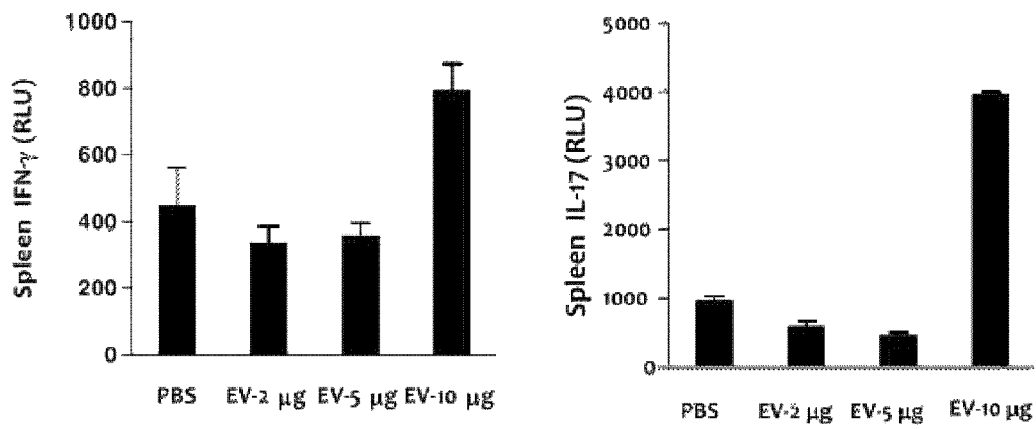
FIG. 43 is of graphs showing elevated levels of IFN-γ와 IL-17 in the mouse splenocytes obtained after immunization was conducted according to the protocol of FIG. 42.

FIG. 43 shows the induction of T cell immune responses by the extracellular vesicles. In this connection, immune cells isolated from the spleen were cultured in vitro for 72 hours and the culture media were analyzed for cytokine content. As can be seen, IFN-γ and IL-17 that are secreted respectively from Th1 and Th17 cells were detected at significantly increased levels in the group administered with the extracellular vesicles (10 µg).

From the data, it can be understood that *Staphylococcus aureus* extracellular vesicles can be used as a vaccine to induce Th1- and Th17-mediated defense against bacterial infections as well as the production of IgG antibody, essential for humoral immunity, thereby effectively preventing diseases caused by *Staphylococcus aureus* and bacterial extracellular vesicles.

Example 23

Figure 44:
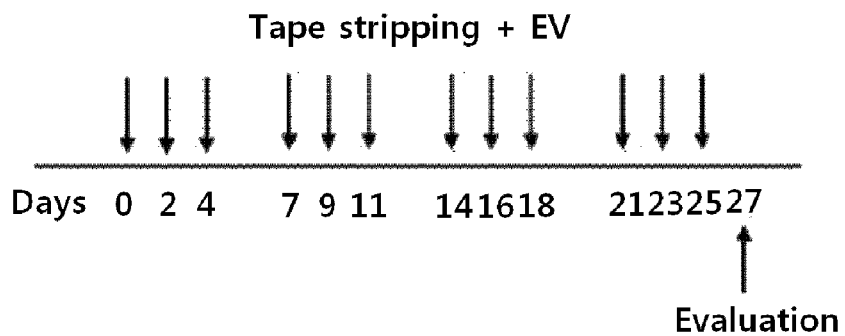
FIG. 44 is a diagram showing a protocol for applying *Staphylococcus aureus*-derived extracellular vesicles once a week for four weeks via a patch to the tape-stripped mouse skin.
Figure 45:
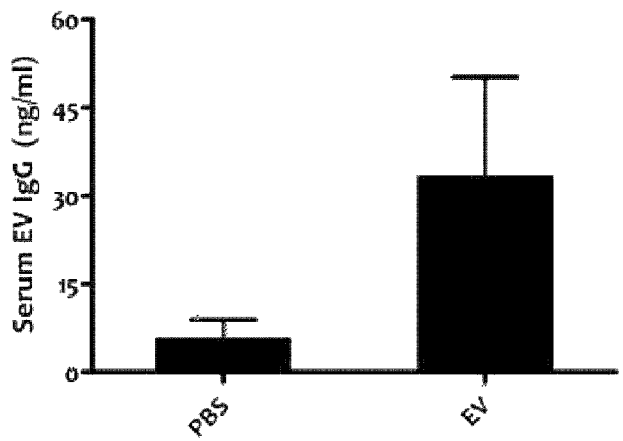
FIG. 45 is a graph showing serum IgG antibody levels after the *Staphylococcus aureus*-derived extracellular vesicles were transdermally administered according to the protocol of FIG. 42, wherein the transdermal administration of the *Staphylococcus aureus*-derived extracellular vesicles greatly induced the production of *Staphylococcus aureus*-derived extracellular vesicle-specific IgG antibodies, as compared to the control.

Induction of Antibody Production and T Cell Immune Response Upon Transdermal Administration (Patch) of *Staphylococcus aureus*-Derived Extracellular Vesicles Immunity induction by transdermal administration of the *Staphylococcus aureus*-derived extracellular vesicles was evaluated. To this end, 5 µg of the *Staphylococcus aureus*-derived extracellular vesicles prepared in Example 13 was administered for 4 weeks using a patch (FIG. 44). FIG. 45 is a graph showing serum IgG antibody levels after the *Staphylococcus aureus*-derived extracellular vesicles were transdermally administered. As shown in the graph, the transdermal administration of the *Staphylococcus aureus*-derived extracellular vesicles greatly induced the production of *Staphylococcus aureus*-derived extracellular vesicle-specific IgG antibodies, as compared to PBS.

To evaluate *Staphylococcus aureus-extracellular* vesicle-induced T cell immune responses, immune cells were separated from the spleen and incubated in vitro for 24 hours with 0.1 μg/ml *Staphylococcus aureus*-derived extracellular vesicles, and the culture media were analyzed for cytokine content. The results are depicted in FIG. 46.

Figure 46:
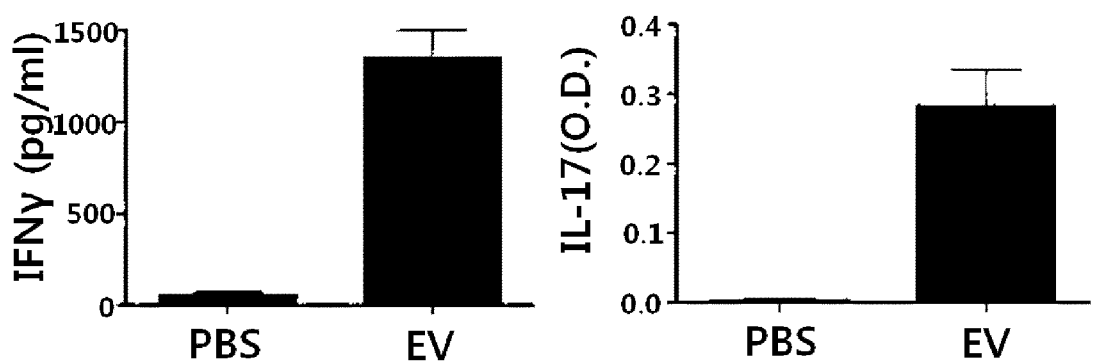
FIG. 46 is of photographs showing that the levels of Th1 and Th17 cytokines in splenocytes were increased in response to the stimulation of *Staphylococcus aureus*-derived extracellular vesicles after mice were treated with the vesicles according to the protocol of FIG. 42.

As is apparent from the data of FIG. 46, the levels of IFN-γ and IL-17 that are secreted respectively from Th1 and Th17 cells were greatly increased over those of the PBS-administered group.

Thus, Th1- and Th17-mediated immunity against *Staphylococcus aureus*-derived extracellular vesicles can be induced by the administration of *Staphylococcus aureus*-derived extracellular vesicles. Therefore, *Staphylococcus aureus*-derived extracellular vesicles, even when administered transdermally, elicit T cell-mediated immunity as well as the production of antibodies, so that they can be used for preventing or treating *Staphylococcus aureus* infections and diseases caused by the extracellular vesicles derived from the bacteria.

Example 24

Induction of Antibody Production and T Cell Immune Response by Combined Administration of *Staphylococcus aureus*-Derived Extracellular Vesicles and Immunostimulant (polyI:C)

Figure 47:
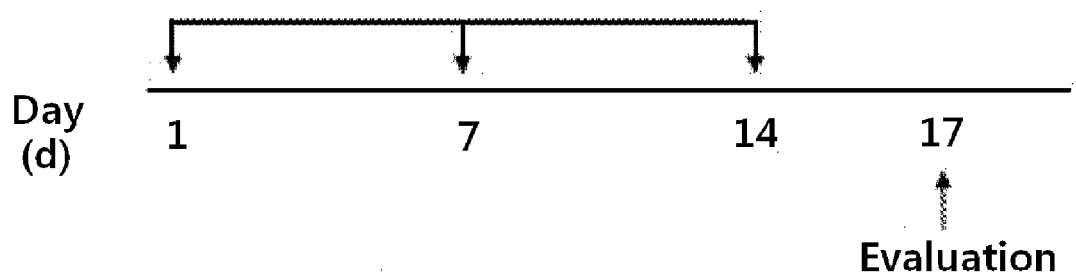
FIG. 47 is a diagram showing a protocol for evaluating immune indices in the mice challenged with *Staphylococcus* after immunization with a combination of *Staphylococcus aureus*-derived extracellular vesicles and polyI:C.

The *Staphylococcus aureus*-derived extracellular vesicles prepared in Example 2 were intraperitoneally injected at a dose of 5 μg alone or in combination with 20 μg of the synthetic dsRNA polyinosinic-polycytidylic acid (polyI:C) three times at regular intervals of one weeks to mice (C57B6, male). Day 7 and 9 after the final immunization, the mice were infected with *Staphylococcus aureus* ($2.4 \times 10^8$ cells) by intraperitoneal injection (FIG. 47). Blood samples were taken, allowed to coagulate at room temperature for 30 min, and centrifuged at 4° C. and 3,500×g for 10 min to obtain sera as supernatants.

Figure 48:
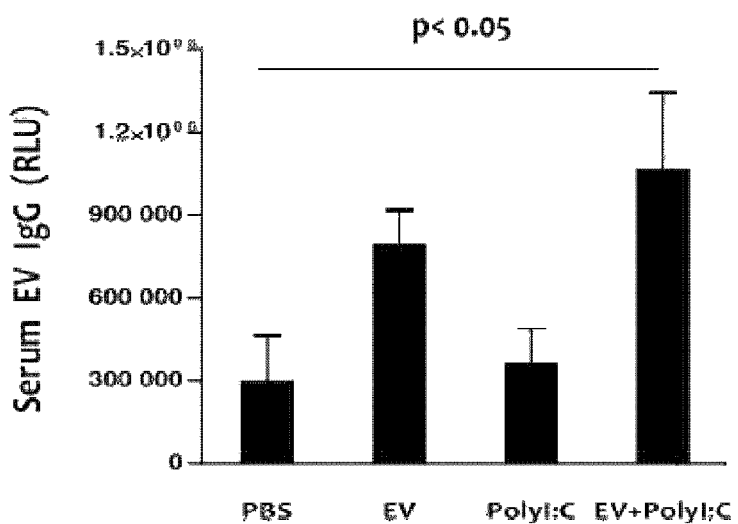
FIG. 48 is a graph showing elevated levels of extracellular vesicle-specific IgG antibodies in the mouse sera obtained according to the protocol of FIG. 47.

FIG. 48 is a graph showing levels of IgG antibody, an index for immune response to the extracellular vesicles, as measured by ELISA. As can be seen, the combined injection of *Staphylococcus aureus*-derived extracellular vesicles and polyI:C induced higher levels of antibodies specific for proteins present in *Staphylococcus aureus* or its vesicles.

Figure 49:
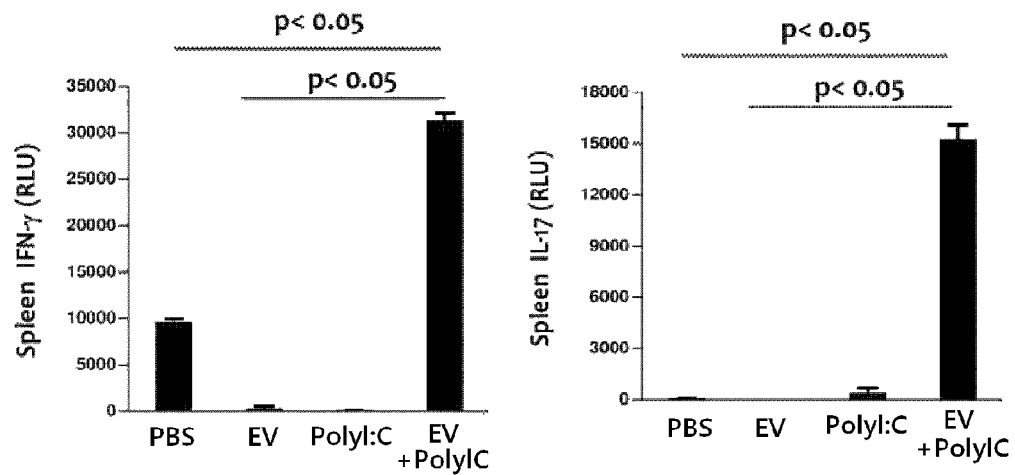
FIG. 49 is a graph showing elevated levels of IFN-γ and IL-17 in mouse splenocytes obtained according to the protocol of FIG. 47.

To evaluate the T cell immune responses induced by the combined administration of *Staphylococcus aureus*-derived extracellular vesicles and polyI:C, immune cells were separated from the spleen and incubated in vitro for 72 hours, and the culture media were analyzed for cytokine content. The results are depicted in FIG. 49. As is apparent from the data of FIG. 49, the levels of IFN-γ and IL-17 that are secreted respectively from Th1 and Th17 cells were greatly increased in the group co-administered with *Staphylococcus aureus*-derived extracellular vesicles and polyI:C, compared to the other groups.

From these results, it can be gleaned that the administration of *Staphylococcus aureus* extracellular vesicles in combination with an immunostimulant such as poly I:C more effectively induces IgG antibody production for humoral immunity as well as Th1- and Th17-mediated immune responses against bacterial infections than does the vesicular vaccine alone, so that the vesicular vaccine in combination with an immunostimulant can be used for preventing *Staphylococcus aureus* infections and diseases caused by the bacterial extracellular vesicles.

Example 25

Figure 50:
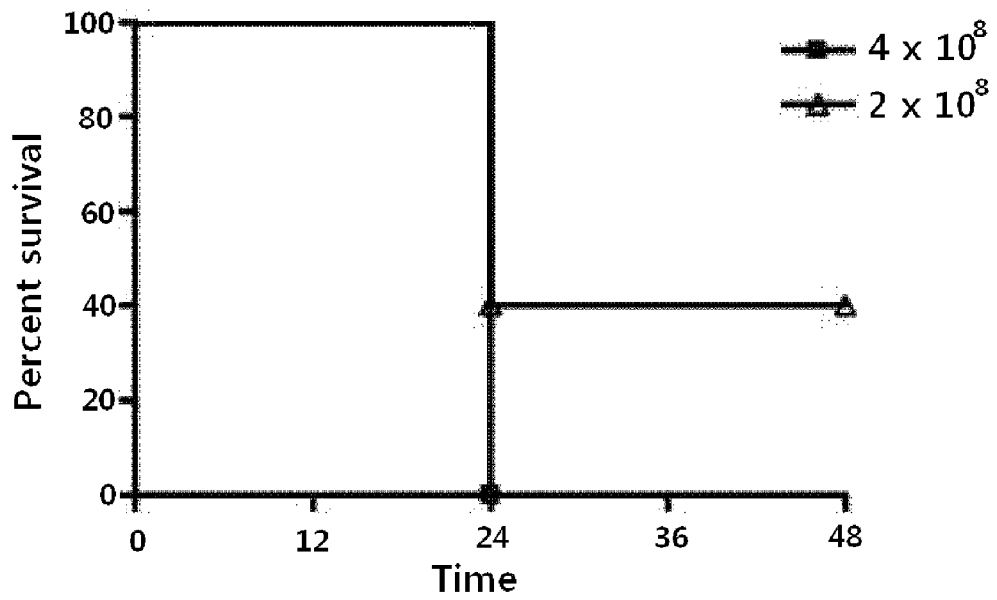
FIG. 50 is a graph showing survival rates of the mice to which two different doses of *Staphylococcus aureus* were intranasally administered.

Pharmaceutical Efficacy of a Combination of *Staphylococcus aureus*-Derived Extracellular Vesicle Vaccine and polyI:C in Animal Model of *Staphylococcus aureus*-Induced Pneumonia In order to establish animal models of *Staphylococcus aureus-induced* pneumonia, *Staphylococcus aureus* was administered at a dose of $4 \times 10^8$ or $2 \times 10^8$ CFU to mice by intranasal inhalation, and survival rates were examined. All mice were dead 24 hours after the administration of $4 \times 10^8$ CFU whereas the rate of survival of mice administered with $2 \times 10^8$ CFU was 40% (FIG. 50).

Figure 51:
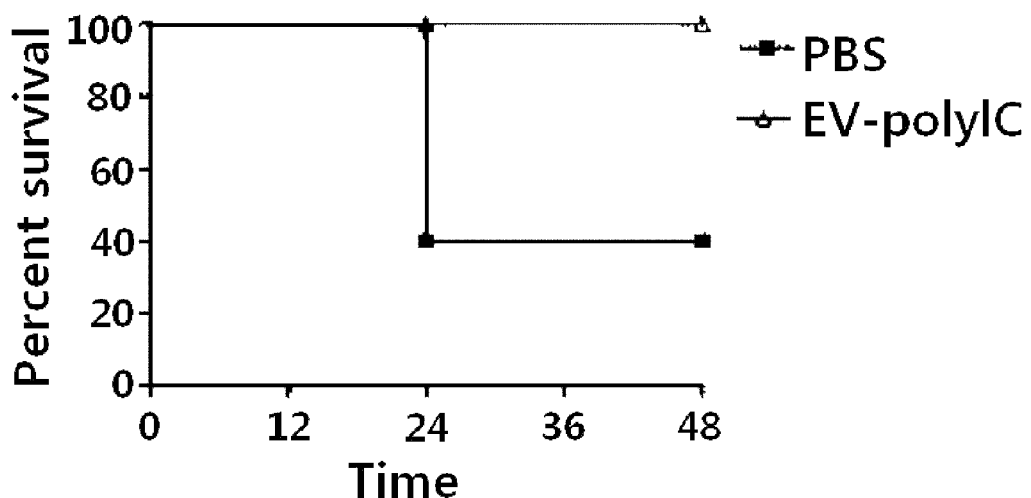
FIG. 51 is a graph showing an elevated survival rate of the mice in which pneumonia was generated by *Staphylococcus* after they were immunized with a combination of *Staphylococcus aureus*-derived extracellular vesicles and polyI:C.

To confirm the effect of the vascular vaccine on the animal model of *Staphylococcus aureus-induced* pneumonia, mice were intraperitoneally injected three times with 5 μg of *Staphylococcus aureus*-derived extracellular vesicles and 20 μg of polyI:C together as in Example 23 and then challenged with $2 \times 10^8$ CFU of *Staphylococcus aureus* by intranasal inhalation, and their survival rates were monitored. Twenty four hours after the challenge, the survival rate of the mice was observed to be 100% when immunized with the vesicular vaccine, but the survival rate decreased to 40% in the mice which had not been immunized (FIG. 51).

These data demonstrate that the vesicular vaccine can very effectively prevent *Staphylococcus aureus-induced* pneumonia and death.

Example 26

Induction of Antibody Production and T Cell Immune Response by Intraperitoneal Injection of *Enterococcus faecalis*-Derived Extracellular Vesicles Extracellular vesicles were isolated from *Enterococcus faecalis* as described in Example 2. To evaluate the *Enterococcus faecalis*-derived extracellular vesicles as a vaccine to induce immune responses, the *Enterococcus faecalis*-derived extracellular vesicles were intraperitoneally injected at a dose of 5 or 10 μg into mice (C57B6, male) two times at regular intervals of one week. Immune responses were evaluated 72 hours after the final injection.

Figure 52:
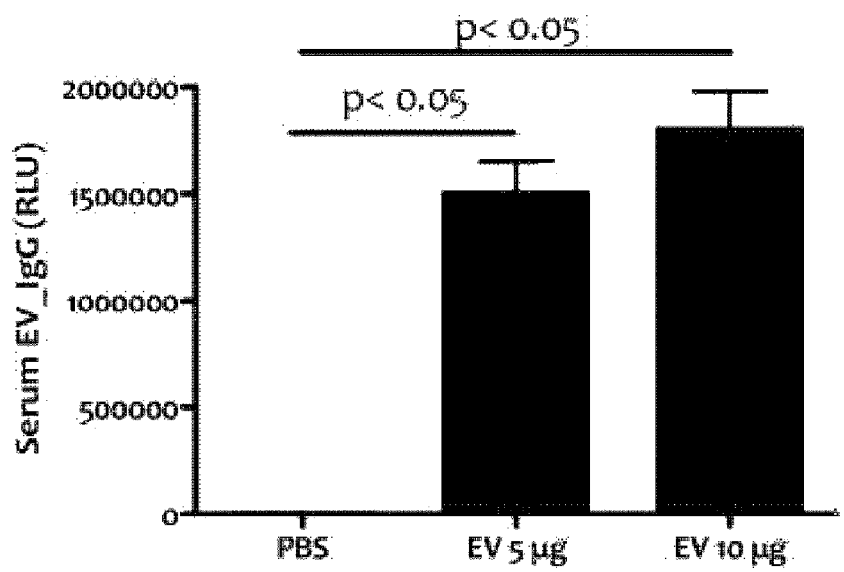
FIG. 52 is a graph showing elevated levels of vesicle-specific IgG antibodies in sera obtained after *Enterococcus faecalis*-derived extracellular vesicles were administered to the mice.

Blood samples were taken, allowed to coagulate at room temperature for 30 min, and centrifuged at 4° C. and 3,500×g for 10 min to take sera as a supernatant. FIG. 52 is a graph in which ELISA levels of IgG antibody, an index for immune response to the extracellular vesicles, are plotted versus doses of vaccine, showing that antibodies specific for vesicular proteins were produced by two intraperitoneal injections of the extracellular vesicles.

To evaluate the T cell immune responses induced by the administration of *Enterococcus faecalis*, immune cells were separated from the spleen after injection of the vesicles, and incubated in vitro for 72 hours, and the culture media were analyzed for cytokine content. The results are depicted in FIG. 53.

Figure 53:
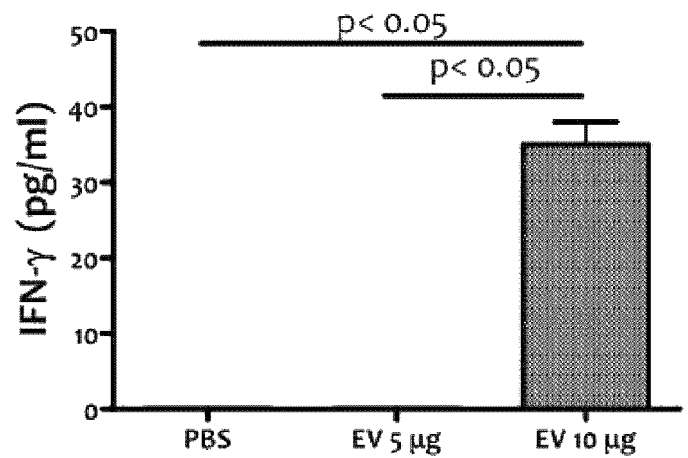
FIG. 53 is a graph showing elevated levels of IFN-γ in the splenocytes obtained after *Enterococcus faecalis*-derived extracellular vesicles were administered to the mice.

As is apparent from the data of FIG. 53, the levels of IFN-γ that are secreted from Th1 cells were greatly increased in the group administered with the extracellular vesicles (10 μg), compared to the other groups.

From the data, it can be understood that *Enterococcus faecalis*-derived extracellular vesicles can be used as a vaccine to induce Th1-mediated defense against bacterial infections as well as the production of IgG antibody, essential for humoral immunity, thereby effectively preventing *Enterococcus faecalis* infections and diseases caused by the bacterial extracellular vesicles.

Example 27

Genetic Analysis of 16S rRNA and DNA of *Staphylococcus aureus*-Derived Extracellular Vesicles PCR (Polymerase Chain Reaction) was performed on *Staphylococcus aureus* and *Staphylococcus aureus*-derived extracellular vesicles (0.2, 0.5, 1.0 µg) using primers for 16S rRNA of *Staphylococcus* (Forward: AGCTTGCTTCTCTGATGTTA, Reverse: TTTCACTTTTGAACCATGCG) [95° C., 5 min—(94° C., 30 s—46° C., 30 s, 72° C., 20 s)×35 cycle—72° C., 7 min—-4° C.]*E. coli* was used as a negative control under the same conditions. Reverse transcription-PCR and PCR products were identified by electrophoresis on 2% agarose gel. The result is depicted in FIG. 54.

Figure 54:
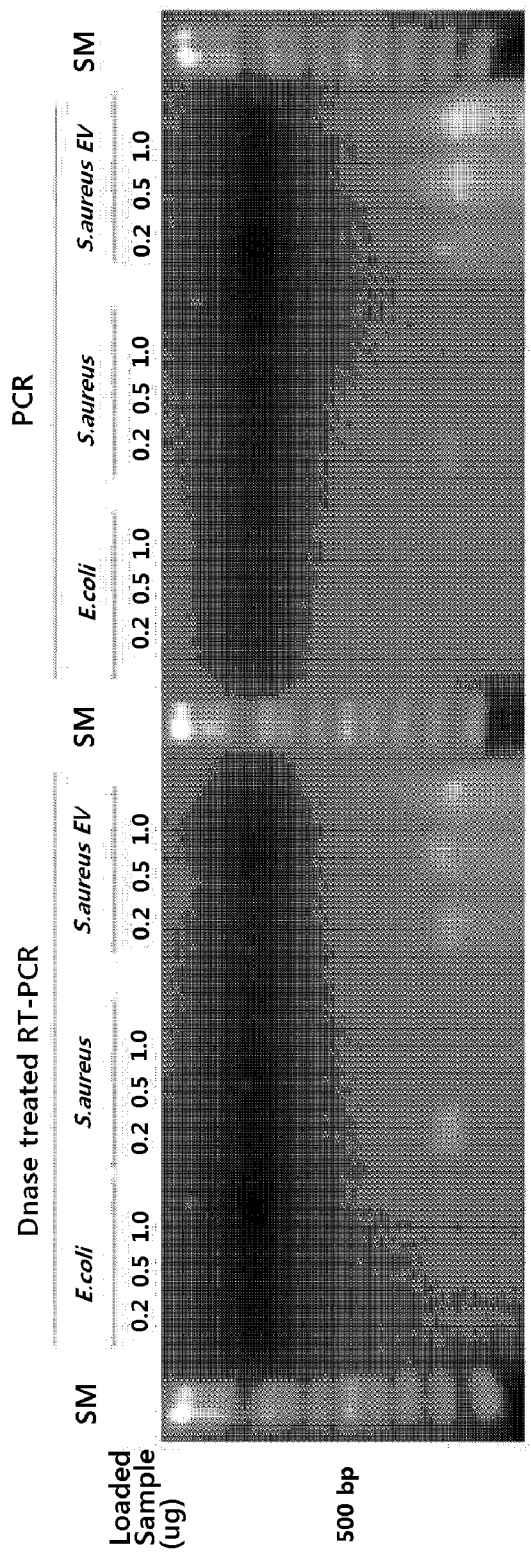
FIG. 54 is a photograph showing the presence of 16S rRNA and DNA within the extracellular vesicles as analyzed by RT-PCR and PCR, respectively.

As shown in FIG. 54, bands were read at 120 bp, demonstrating the presence of RNA and DNA in the *Staphylococcus aureus*-derived extracellular vesicles.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

The Gram-positive bacteria-derived extracellular vesicles of the present invention can be used to establish disease animal models that allow the effective discovery of drugs preventive or therapeutic of Gram-positive bacteria-derived extracellular vesicle-induced diseases. Also, Gram-positive bacteria-derived extracellular vesicles themselves or their modifications may be used to develop vaccines against Gram-positive bacteria infections or Gram-positive bacteria-derived extracellular vesicle-caused diseases. Further, the Gram-positive bacteria-derived extracellular vesicles can be applied to the development of a method for diagnosing pathogenic factors responsible for the onset of Gram-positive bacteria-derived extracellular vesicle-caused diseases.

The invention claimed is:

1. A method of causing to induce antibody production or a T cell immune response against Gram-positive bacteria, the method comprising:
    isolating extracellular vesicles from Gram-positive bacteria with a cell wall, the extracellular vesicles comprising a biological substance of the Gram-positive bacteria; and
    providing a composition comprising extracellular vesicles and a pharmaceutically acceptable carrier for administering the composition to a subject in need of such induction at a sublethal dose,
    wherein isolating comprises:
        culturing Gram-positive bacteria in a culture medium,
        obtaining supernatant of the culture medium by centrifugation, and
        filtering the supernatant with a filter having a pore size sufficient to isolate extracellular vesicles contained in the supernatant.

2. The method of claim 1, wherein the Gram-positive bacteria comprise bacteria of Firmicutes phylum.

3. The method of claim 1, wherein the Gram-positive bacteria comprise bacteria of a genus selected from the group consisting of *Staphylococcus, Streptococcus, Enterococcus, Bacillus, Corynebacterium, Norcardia, Clostridium, Actinobacteria* and *Listeria*.

4. The method of claim 1, wherein the Gram-positive bacteria are selected from the group consisting of *Enterococcus faecalis, Staphylococcus aureus, Staphylococcus epidermidis*, and *Bacillus subtilis*.

5. The method of claim 1, wherein the Gram-positive bacteria comprise bacteria of Mollicutes class.

6. The method of claim 1, wherein the Gram-positive bacteria comprise *Mycoplasma*.

7. The method of claim 1, wherein the Gram-positive bacteria comprise transformed bacteria.

8. The method of claim 1, wherein the extracellular vesicles contain a drug or an immunostimulant.

9. The method of claim 1, wherein the biological substance comprises proteins of the Gram-positive bacteria.

10. The method of claim 1, wherein the administration is selected from the group consisting of dermal administration, intravenous injection, intranasal administration, sublingual administration, intratracheal inhalation, oral administration, and intrarectal administration.

11. The method of claim 1, wherein the subject is in need of treating or inhibiting a disease selected from the group consisting of a dermal disease, a respiratory disease, a digestive disease, a genital disease, a vascular disease, a metabolic disease, a lung disease, a bone disease, and a cranial nerve disease.

12. The method of claim 1, wherein the subject is in need of treating or inhibiting skin infection, respiratory infection, urogenital infection, bone infection, central nervous system infection, and sepsis.

13. The method of claim 1, wherein the subject is in need of treating or inhibiting a disease selected from the group consisting of sepsis, Pneumonia and atopic dermatitis.

14. The method of claim 1, wherein the method causes to induce IgG antibody production.

15. The method of claim 1, wherein the method causes to induce Th1- and Th7-mediated immune response.

16. The method of claim 1, the method causes to induce production of IFN-γ and IL-17.

17. The method of claim 1, wherein the pore size is 0.22 µm.

* * * * *